(12) United States Patent
Gong et al.

(10) Patent No.: US 7,914,985 B2
(45) Date of Patent: Mar. 29, 2011

(54) ALANINE TRANSAMINASE ENZYMES AND METHODS OF USE

(75) Inventors: Da-Wei Gong, Olney, MD (US); Alan R. Shuldiner, Columbia, MD (US); Rong-Ze Yang, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1012 days.

(21) Appl. No.: 11/587,331

(22) PCT Filed: Apr. 19, 2005

(86) PCT No.: PCT/US2005/013019
§ 371 (c)(1),
(2), (4) Date: Apr. 20, 2007

(87) PCT Pub. No.: WO2005/113761
PCT Pub. Date: Dec. 1, 2005

(65) Prior Publication Data
US 2008/0220417 A1    Sep. 11, 2008

(51) Int. Cl.
*C12Q 1/68*   (2006.01)
*C12N 9/10*   (2006.01)
*C07H 21/04*  (2006.01)

(52) U.S. Cl. ........ 435/6; 435/193; 435/320.1; 435/69.1; 536/23.2

(58) Field of Classification Search ........................ None
See application file for complete search history.

(56) References Cited

U.S. PATENT DOCUMENTS
4,554,101 A    11/1985    Hopp

FOREIGN PATENT DOCUMENTS
| JP | 050-68548 | | 3/1993 |
| JP | 10-075787 | * | 3/1998 |
| WO | WO 02/08400 A2 | | 1/2002 |
| WO | WO 02/55712 A2 | | 7/2002 |
| WO | WO 02/092768 A2 | | 11/2002 |

OTHER PUBLICATIONS

SCORE search results from PCT/US2005/13019.*
Q8BGT5 (ALAT2_MOUSE) UniProtKB/Swiss-Prot First appeared on Mar. 2003.*
Q8K1J3_MOUSE accession Q8K1J3 Glutamic pyruvate transaminase (alanine aminotransferase 2 created on Oct. 1, 2002.*
Mariko Ishiguro Complete Amino Acid Sequence of Rat Liver Cytosolic Alanine Aminotransferase. Biochemistry 30, 6048-6053, 1991.*
Database UNIPROT, accession No. P25409, Alanine Aminotransferase, May 1, 1992, retrieved from PIR, 099.8% identity in 495 amino acid overlap with SEQ ID No. 6.
Mariko Ishiguro et al.: *Complete Amino Acid Sequence of Rat Liver Cytosolic Alanine Aminotransferase*. Biochemistry 1991; vol. 30 No. 24: pp. 6048-6053.
Yang R.-Z, et al. *cDNA Cloning, Genomic Structure, Chromosomal Mapping, and Functional Expression of a Novel Human Alanine Aminotransferase*, Genomics, 2002, 79, 445-450.

* cited by examiner

*Primary Examiner* — Manjunath N Rao
*Assistant Examiner* — Kagnew H Gebreyesus
(74) *Attorney, Agent, or Firm* — Pauley Petersen & Erickson

(57) ABSTRACT

Novel alanine transaminase (ALT) polypeptides and the use thereof as a diagnostic marker to predict and monitor tissue damage and/or tissue malfunction. The ALT polypeptides are murine and/or *rattus* ALT polypeptides and said ALT polypeptides are used to detect, predict and/or determine hepatic processes of an animal, particularly mice and/or rats.

5 Claims, 6 Drawing Sheets

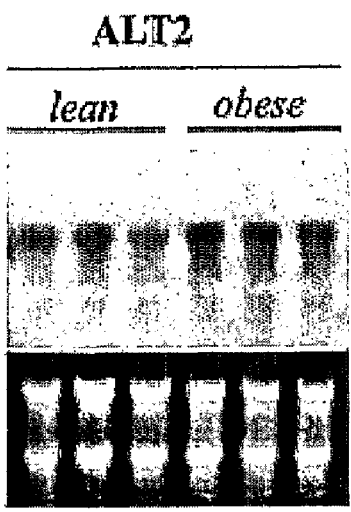
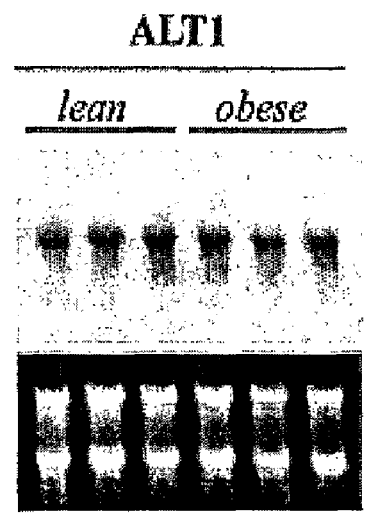
FIG 4A  FIG. 4B
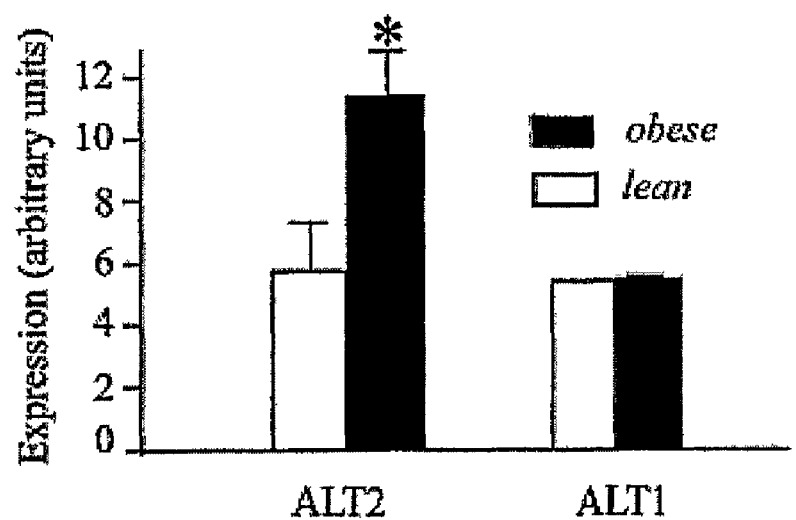
FIG. 4C

```
                   1                                                                              80
SEQ ID NO:6                          MAS RVNDQSQASR NGLKGKVLTL DTMNPCVRRV EYAVRGPIVQ RALELEQELR
SEQ ID NO:1                          MAS QRNDRIQASR NGLKGKVLTL DTMNPCVRRV EYAVRGPIVQ RALELEQELR
hGPT1                                MAS STGDRSQAVR HGLRAKVLTL DGMNPRVRRV EYAVRGPIVQ RALELEQELR
SEQ ID NO:5  MQRAAVLVRR GSCPRASGPW GRSHSSAAAE ASAALKVRPE RSPRDRILTL ESMNPQVKAV EYAVRGPIVL KAGEIEMELQ
SEQ ID NO:2  MQRAAVLVRR GSCPRASGPW GRSHSSAAAE ASAALKVRPE RSPRDRILTL ESMNPQVKAV EYAVRGPIVL KAGEIEMELQ
hALT2        MQRAAALVRR GCGPRTPSSW GRSQSSAAAE ASAVLKVRPE RSRRERILTL ESMNPQVKAV EYAVRGPIVL KAGEIELELQ
Consensus    .......... .......... .......aAe asadlkqapr rglr.r!LTL #sMNPqVraV EYAVRGPIVq rAgEiEqELr 81                                                                             160
SEQ ID NO:6  QGVKKPFTEV IRANIGDAQA MGQRPITFFR QVLALCVYPN LLSSPDFPED AKRRAERILQ ACGGHSLGAY SISSGIQPIR
SEQ ID NO:1  QGVKKPFTEV IRANIGDAQA MGQRPITFFR QVLALCVYPN LLSSPDFPED AKRRAERILQ ACGGHSLGAY SISSGIQPIR
hGPT1        QGVKKPFTEV IRANIGDAQA MGQRPITFLR QVLALCVNPD LLSSPNFPDD AKKRAERILQ ACGGHSLGAY SVSSGIQLIR
SEQ ID NO:5  RGIKKPFTEV IRANIGDAHA MGQQPITFLR QVMALCTYPN LLNSPSFPED AKKRARRILQ ACGGNSLGSY SASQGVNCIR
SEQ ID NO:2  RGIKKPFTEV IRANIGDAHA MGQQPITFLR QVMALCTYPN LLNSPSFPED AKKRARRILQ ACGGNSLGSY SASQGVNCIR
hALT2        RGIKKPFTEV IRANIGDAQA MGQQPITFLR QVMALCTYPN LLDSPSFPED AKKRARRILQ ACGGNSLGSY SASQGVNCIR
Consensus    rG!KKPFTEV IRANIGDAqA MGQrPITF1R QV$ALCtyP# LLsSPsFP#D AKkRArRILQ ACGGnSLGaY SaSqG!#cIR 161                                                                             240
SEQ ID NO:6  EDVAQYIERR DGGIPADPNN IFLSTGASDA IVTMLKLLVS GEGRARTGVL IPIPQYPLYS AALAELDAVQ VDYYLDEERA
SEQ ID NO:1  EDVAQYIERR DGGIPADPNN IFLSTGASDA IVTMLKLLVA GEGRARTGVL IPIPQYPLYS AALAELDAVQ VDYYLDEERA
hGPT1        EDVARYIERR DGGIPADPNN VFLSTGASDA IVTVLKLLVA GEGHTRTGVL IPIPQYPLYS ATLAELGAVQ VDYYLDEERA
SEQ ID NO:5  EDVAAFITRR DG-VPADPDN IYLTTGASDG ISTILKLLVS GGGKSRTGVM IPIPQYPLYS AVISELDAIQ VNYYLDEDNC
SEQ ID NO:2  EDVAAFITRR DG-VPADPDN IYLTTGASDG ISTILKLLVS GGGKSRTGVM IPIPQYPLYS AVISELDAVQ VNYYLDEENC
hALT2        EDVAAYITRR DGGVPADPDN IYLTTGASDG ISTILKILVS GGGKSRTGVM IPIPQYPLYS AVISELDAIQ VNYYLDEENC
Consensus    EDVAa%IeRR DGg!PADP#N !%LsTGASDa IsTiLK1lLVs GeGksRTGV$ IPIPQYPLYS AviaELdA!Q V#YYLDE#ra 241                                                                             320
SEQ ID NO:6  WALDIAELRR ALCQARDRCC PRVLCVINPG NPTGQVQTRE CIEAVIRFAF KEGLFLMADE VYQDNVYAEG SQFHSFKKVL
SEQ ID NO:1  WALDIAELRR ALCQARDRCC PRVLCVINPG NPTGQVQTRE CIEAVIRFAF EEGLFLMADE VYQDNVYAAG SQFHSFKKVL
hGPT1        WALDVAELHR ALGQARDHCR PRALCVINPG NPTGQVQTRE CIEAVIREAF EERLFLLADE VYQDNVYAAG SQFHSFKKVL
SEQ ID NO:5  WALNVDELRR ALRQAKDHCD PKVLCIINPG NPTGQVQSRK CIEDVIHFAW EEKLFLIADE VYQDNVYSPD CRFHSFKKVL
SEQ ID NO:2  WALNVDELRR ALRQAKDHCD PKVLCIINPG NPTGQVQSRK CIEDVIHFAW EEKLFLLADE VYQDNVYSPD CRFHSFKKVL
hALT2        WALNVNELRR AVQEAKDHCD PKVLCIINPG NPTGQVQSRK CIEDVIHFAW EEKLFLLADE VYQDNVYSPD CRFHSFKKVL
Consensus    WAL#!aELrR Al.#ArDhCd PrvLC!INPG NPTGQVQsRe CIEaVIrFAf eEkLFL$ADE VYQDNVYapd crFHSFKKVL 321                                                                             400
SEQ ID NO:6  MEMGPPYSTQ QELASFHSVS KGYMGECGFR GGYVEVVNMD AEVQKQMGKL MSVRLCPPVP GQALMDMVVS PPTPSEPSFK
SEQ ID NO:1  TEMGPPYATQ QELASFHSVS KGYMGECGFR GGYVEVVNMD AEVQKQMAKL MSVRLCPPVP GQALMGMVVS PPTPSEPSFK
hGPT1        MEMGPPYAGQ QELASFHSTS KGYMGECGFR GGYVEVVNMD AAVQQQMLKL MSVRLCPPVP GQALLDLVVS PPAPTDPSFA
SEQ ID NO:5  YQMGPPEYSSN VELASFHSTS KGYMGECGYR GGYMEVINLH PEIKGQLVKL LSVRLCPPVS GQAAMDIVVN PPVPGEESFE
SEQ ID NO:2  YQMGHEYSSN VELASFHSTS KGYMGECGYR GGYMEVINLH PEIKGQLVKL LSVRLCPPVS GQAAMDIVVN PPEPGEESFE
hALT2        YEMGPEYSSN VELASFHSTS KGYMGECGYR GGYMEVINLH PEIKGQLVKL LSVRLCPPVS GQAAMDIVVN PPVAGEESFE
Consensus    y#MGpeYss# qELASFHStS KGYMGECG%R GGYmEV!N$d ae!qgQ$vKL $SVRLCPPVp GQAa$dIVVn PP.pg#eSFe 401                                                                             480
SEQ ID NO:6  QFQAERQEVL AELAAKAKLT EQVFNEAPGI RCNPVQGAMY SFPQVQLPLK AVQRAQELGL APDMFFCLCL LEETGICVVP
SEQ ID NO:1  QFQAERQEVL AELAAKAKLT EQVFNEAPGI RCNPVQGAMY SFPQIQLPLK AVQRAQELGL APDMFFCLCL LEETGICVVP
hGPT1        QFQAEKQAVL AELAAKAKLT EQVFNEAPGI SCNPVQGAMY SFPRVQLPPR AVERAQELGL APDMFFCLRL LEETGICVVP
SEQ ID NO:5  QFTREKESVL GNLAKKAKLT EDLFNQVPGI QCNPLQGAMY AFPRILIPAK AVEAAQSHKM APDMFYCMKL LEETGICVVP
SEQ ID NO:2  QFSREKEFVL GNLAKKAKLT EDLFNQVPGI QCNPLQGAMY AFPRILIPAK AVEAAQSHKM APDMFYCMKL LEETGICVVP
hALT2        QFSREKESVL GNLAKKAKLT EDLFNQVPGI HCNPLQGAMY AFPRIFIPAK AVEAAQHQM APDMFYCMKL LEETGICVVP
Consensus    QFqaEk#.VL a#LAaKAKLT E#1FN#aPGI .CNP1QGAMY aFPr!qiPak AV#aAQ.hg$ APDMF%C$kL LEETGICVVP 481              523
SEQ ID NO:6  GSGFGQQEGT YHFRMTILPP MEKLRLLLEK LSHFHAKFTH EYS
SEQ ID NO:1  GSGFGQQEGT YHFRMTILPP MEKLRVLLEK LRHFHAKFTH EYS
hGPT1        GSGFGQREGT YHFRMTILPP LEKLRLLLEK LSRFHAKFTL EYS
SEQ ID NO:5  GSGFGQREGT YHFRMTILPP VEKLKTVLHK VKDFHLKFLE KYS
SEQ ID NO:2  GSGFGQREGT YHFRMTILPP VDKLKTVLHK VKDFHLKFLE QYS
hALT2        GSGFGQREGT YHFRMTILPP VEKLKTVLQK VKDFHINFLE KYA
Consensus    GSGFGQrEGT YHFRMTILPP v#KLrt1LeK lkdFHakFle eYs
```

FIG. 6

ALANINE TRANSAMINASE ENZYMES AND METHODS OF USE

GOVERNMENT INTEREST

This work was supported in part by grant R03 DK60563-01 from the National Institutes of Health. The U.S. Government has certain rights to this invention.

CROSS REFERENCE TO RELATED APPLICATION

This application claims priority from U.S. provisional patent application Ser. No. 60/563,389, filed on 19 Apr. 2004, and U.S. provisional patent application Ser. No. 60/588,126, filed on 15 Jul. 2004. The priority provisional patent applications are hereby incorporated by reference herein in their entirety and are made a part hereof, including but not limited to those portions which specifically appear hereinafter.

FIELD OF THE INVENTION

This invention relates to alanine transaminase (ALT) polypeptides and the use thereof as a diagnostic marker to predict and monitor tissue damage and/or tissue malfunction. More specifically, the ALT polypeptides are murine and/or *rattus* ALT polypeptides and said ALT polypeptides are used to detect, predict and/or determine hepatic processes of an animal, particularly mice and/or rats. The present invention additionally relates to assays for the ALT polypeptides to diagnose tissue damage and/or tissue malfunction having a range of etiologies that include but are not limited to hepatitis, nonalcoholic steatohepatitis (NASH), fatty liver, cirrhosis, and drug hepatotoxicity, and other disorders in muscle, brain, kidney, and adipose tissue, particularly in mice and/or rats.

BACKGROUND OF THE INVENTION

Alanine transaminase (ALT) [EC 2.6.1.2., also known as glutamate pyruvate transaminase (GPT) and alanine aminotransferase] is a pyridoxal enzyme catalyzing reversible transamination between alanine and 2-oxoglutarate to form pyruvate and glutamate. By mediating the conversion of these four major intermediate metabolites, ALT plays an important role in gluconeogenesis and amino acid metabolism. In muscle and certain other tissues, ALT degrades amino acids for fuel, and amino groups are collected from glutamate by transamination. ALT transfers the α-amino group from glutamate to pyruvate to form alanine, which is a major amino acid in blood during fasting. Alanine is taken up by the liver for generating glucose from pyruvate in a reverse ALT reaction, constituting the so-called alanine-glucose cycle. This cycle is also important during intensive exercise when skeletal muscles operate anaerobically, producing not only ammonia groups from protein breakdown but also large amounts of pyruvate from glycolysis.

ALT activities exist in many tissues, including liver, muscle, heart, kidney, and brain. Molecular cloning of the complementary DNAs (cDNAs) of two human ALT isoenzymes, hALT1 and hALT2 have been disclosed in International Publication WO 02/092768, herein fully incorporated by reference in its entirety. The independent DNA encoding for the two human ALT isoenzymes (gpt1 and gpt2, respectively) has been shown to be localized to separate chromosomes in humans, and that they have distinctive tissue distribution patterns, suggesting a tissue-dependent role for ALT isoenzymes.

Perhaps the most well-known aspect of ALT is that it is used clinically as an index of liver integrity or hepatocellular damage. Serum ALT activity is significantly elevated in a variety of liver damage conditions including viral infection, alcoholic steatosis, nonalcoholic steatohepatitis (NASH), and drug toxicity, although the underlying mechanism is generally not well understood. While low level of ALT is present in peripheral circulation because of normal cell turnover or release from nonvascular sources, the liver has been shown to contain the highest levels of ALT. The difference between ALT levels in liver and in blood has been shown to be about 2,000-3,000-fold. Hence, the increased ALT in serum, plasma, or blood is regarded as a marker of liver injury because of the "leakage" of hepatic ALT into the circulation. Usually, the nature of liver injury causes the blood ALT levels to vary greatly. Extremely high transaminase levels (greater than 8- to 10-fold normal) can indicate acute viral hepatitis and/or drug-induced hepatotoxicity. A mild chronic increase of serum ALT (2- to 8-fold) is generally a characteristic of chronic hepatitis, fatty liver, and/or steatosis. However, many details of the mechanism for the correlation of ALT levels with the etiology of liver damage remain to be understood.

Even though serum ALT is one of the most widely-used assays in clinical chemistry, there are serious deficiencies with the assay because it is an inadequate predictor in some cases. Recent studies have cast doubt on serum ALT assay's specificity for liver disease. Higher than normal ALT levels are frequently associated with other clinical conditions such as obesity, muscle disease, heart failure, hemochromatosis, Wilson's disease, α1-antitrypsin deficiency.

There is a need for improved ALT immunoassays that more accurately indicate and/or diagnose tissue injury and/or disease. There is a need for an ALT animal model for research and testing purposes. There is also a need for improved animal ALT immunoassays for use in, for example, drug testing and toxicology studies.

SUMMARY OF THE INVENTION

As discussed above, alanine aminotransferase (ALT) is a widely used index of liver integrity or hepatocellular damage in clinics as well as a key enzyme in intermediatary metabolism. Complementary DNAs of murine homologues of human alanine aminotransferase 1 and 2 (mALT1 and mALT2) and of rat homologues of human alanine aminotransferase 1 and 2 (rALT1 and rALT2) have been cloned.

The polypeptides of murine ALT1 (mALT1) and ALT2 (mALT2) of this invention share 87% and 93% identity, respectively, with their human counterparts at the amino acid level. The murine ALT genes of the two murine ALT isoenzymes localize to separate chromosomes, with the murine ALT1 gene (gpt1) on chromosome 15 and the murine ALT2 gene (gpt2) on chromosome 8. The murine gpt1 and gpt2 also differ in messenger RNA expression. The murine gpt1 is mainly expressed in liver, bowel, and white adipose tissue (WAT) and the murine gpt2 is highly expressed in muscle, liver, and white adipose tissue. Expression of recombinant murine ALT1 and murine ALT2 proteins in *Escherichia coli* (*E. coli*) produced functional enzymes that catalyze alanine transamination.

Rat ALT1 polypeptide consists of 496 amino acids and shares 97% and 88% identity to murine and human ALT1, respectively, at the amino acid level. Rat ALT2 polypeptide is composed of 522 amino acids and share 98% and 95% identity to murine and human ALT2, respectively, at the amino acid level. Rat ALT1 and rat ALT2 polypeptides have 68% sequence identity and 77% similarity. The genes of rat ALT1 and ALT2 reside on the chromosome 7 and 19, respectively. A sequence alignment of murine ALT1 and ALT2, human ALT1 and ALT2 and rat ALT1 and ALT2 is provided in FIG. 6.

The diagnostic value of murine ALT isoenzymes in liver disease was determined by an obese animal model. In fatty livers of obese mice, murine ALT2 gene expression is induced 2-fold, but murine ALT1 remains the same. Furthermore, in fatty liver, total hepatic murine ALT activity is elevated significantly by 30% whereas aspartate aminotransferase (AST) activity remains unchanged. Thus, murine ALT2 is responsible for the increased ALT activity in hepatic steatosis and allows for a murine ALT isoenzyme-specific assay having more diagnostic value than total ALT activity assays currently in clinical use. As many pharmaceutical companies do preclinical toxicology experiments in mice by measuring ALT as an indicator of liver toxicity, the murine isoenzyme-specific assays of this invention provide improved assays for assessing preclinical toxicity of new medications.

Another embodiment of the present invention is directed to antibodies, particularly anti-ALT1 antibodies and anti-ALT2 antibodies. In a specific embodiment, the antibody specifically binds to murine ALT1. In another specific embodiment, the antibody specifically binds to murine ALT2. In yet another specific embodiment, the antibody specifically binds to rat ALT1. In still yet another specific embodiment, the antibody specifically binds to rat ALT2.

It is an object of this invention to have a murine ALT polypeptide which has the amino acid sequence of SEQ ID NO:1 (murine ALT1) or an amino acid having about 95% homology thereto. In certain specific embodiments, the amino acid having about 95% homology to SEQ ID NO:1 is SEQ ID NO:6.

It is another object of this invention to have a murine ALT polypeptide which has an amino acid of SEQ ID NO:2 (murine ALT2) or an amino acid having about 95% homology thereto. In certain specific embodiments, the amino acid having about 95% homology to SEQ ID NO:2 is SEQ ID NO:5.

It is another object of this invention to have a polynucleotide which encodes for each of the murine ALT isoenzymes. It is a further object of this invention that the polynucleotide encodes the amino acid sequence of SEQ ID NO:1 and/or SEQ ID NO:2 or an amino acid sequence having about 95% homology to SEQ ID NO:1 and/or SEQ ID NO:2.

It is also further object of this invention that the polynucleotide sequence be the sequence of SEQ ID NO:3 or SEQ ID NO:4. In one embodiment in which the polynucleotide sequence is the polynucleotide sequence encoding for the homolog of SEQ ID NO:1 or SEQ ID NO:2, the polynucleotide sequences are SEQ ID NO:7 (rat ALT1) or SEQ ID NO:8 (rat ALT2).

It is another object of this invention to have a polynucleotide which encodes for each of the rat ALT isoenzymes. It is a further object of this invention that the polynucleotide encodes the amino acid sequence of SEQ ID NO:5 and/or SEQ ID NO:6 or an amino acid sequence having about 95% homology to SEQ ID NO:5 and/or SEQ ID NO:6. It is a further object of this invention that the polynucleotide sequence be the sequence of SEQ ID NO:7 or SEQ ID NO:8.

It is another object of this invention to have an antibody which binds specifically to one of the isoenzymes of ALT and not the other isoenzyme. For example, an antibody of one embodiment of this invention is specific for murine ALT2 and does not bind to murine ALT1. In an alternative embodiment, an antibody of the present invention is specific for rat ALT2 polypeptide and not rat ALT1 polypeptide. In embodiments where a mouse animal model is employed, the antibody of the present invention binds to the murine ALT2 sequence of SEQ ID NO:2 or an ALT2-specific fragment thereof or a homolog of SEQ ID NO:2, or, alternatively, to the protein encoded by the DNA sequence of SEQ ID NO:4 or a murine ALT2-specific fragment thereof.

In an alternative embodiment, such as for use in a rat animal model, an antibody of the present invention specifically binds a rat ALT2 amino acid sequence of SEQ ID NO:5 or a fragment or homolog thereof. In another embodiment, the antibody of the present invention specifically binds a rat ALT1 amino acid sequence of SEQ ID NO:6 or a fragment or homolog thereof.

It is an object of this invention to have an expression vector for each of the ALT isoenzymes. The expression vector can be a plasmid, cosmid, or other type of vector where the DNA sequence encoding for the ALT is operatively linked to expression sequences, such as a promoter. The DNA sequence for murine ALT can be the sequence of SEQ ID NO:3 and/or SEQ ID NO:4, or can be a sequence which encodes for the amino acid sequence of SEQ ID NO:1 and/or SEQ ID NO:2 or a homolog of SEQ ID NO:1 and/or SEQ ID NO:2. The DNA sequence for rat ALT can be the sequence of SEQ ID NO:7 (rALT1) and/or SEQ ID NO:8 (rALT2), or can be a sequence which encodes for the amino acid sequence of SEQ ID NO:5 and/or SEQ ID NO:6 or a homolog of SEQ ID NO:5 and/or SEQ ID NO:6.

It is an object of this invention to have a method for detecting the presence of ALT1 mRNA and/or ALT2 mRNA in a sample. It is a further object of this invention that the sample can be tissue or bodily fluids from a mouse and/or rat. It is a further object of this invention that a polynucleotide probe be used to detect the presence of the ALT1 mRNA and/or the ALT2 mRNA in a sample.

It is an object of this invention to have a method to detect the presence of ALT1 protein and/or ALT2 protein in a sample. It is a further object of this invention that the sample can be tissue or bodily fluids from a mouse and/or a rat. It is another object of this invention that one uses antibodies (monoclonal or polyclonal) that bind specifically to ALT1 or that bind specifically to ALT2 to detect the respective protein. It is another object of this invention that the bodily fluids can be blood, serum, lymph, urine, sweat, mucus, sputum, saliva, semen, spinal fluid, interstitial fluid, synovial fluid, cerebrospinal fluid, gingival fluid, vaginal fluid, and pleural fluid. It is also an object of this invention that the tissue can be liver, brain, muscle, adipose tissue, and kidney.

It is another object of this invention to have a method for diagnosing or detecting injury or disease involving tissue which contains ALT2. It is a further object of this invention that the method involves using antibodies (polyclonal or monoclonal) that specifically bind to a ALT2 polypeptide of the present invention to measure the level of ALT2 in bodily fluids from the animal. It is another object of this invention to use antibodies (polyclonal or monoclonal) that specifically bind to ALT1 to measure the level of ALT1 in bodily fluids from the animal and then to compare the level of ALT2 to ALT1. When the level of ALT2 is sufficiently higher than the level of ALT1 or the level of ALT2 falls within a pre-determined range, then the animal is diagnosed with a specific disease or injury. It is another object of this invention that the bodily fluids can be blood, serum, lymph, urine, sweat, mucus, sputum, saliva, semen, spinal fluid, interstitial fluid, synovial fluid, cerebrospinal fluid, gingival fluid, vaginal fluid, and pleural fluid. Furthermore, the tissue can be liver, brain, muscle, adipose tissue (white adipose tissue "WAT" or brown adipose tissue "BAT"), and kidney.

It is an object of this invention to have a kit useful in diagnosing damage or disease in tissue containing ALT. This kit has a measurer of ALT, either ALT1 or ALT2, levels in a sample of bodily fluids and an indicator for determining if amount of ALT measured by the ALT measurer falls in a range associated with damage or a specific disease in the ALT containing tissue. It is further object of this invention that the kit may also contain a measurer for both ALT1 and ALT2 levels in a sample of bodily fluids and an indicator for determining if amount of each of ALT1 and ALT2 measured by the measurer(s) falls in a range associated with damage or a specific disease in the ALT containing tissue. The ALT1 measurer and the ALT2 measurer can be a biologic assay, an antibody-based assay, an enzyme linked immunosorbent assay, a Western blot, a rapid immunoassay, a radioimmunoassay, and combinations thereof.

It is another object of this invention to have a diagnostic kit useful for diagnosing damage or disease to ALT1 containing tissue and/or ALT2 containing tissue. This diagnostic kit can contain ALT1 specific antibodies (polyclonal or monoclonal), immunoassay reagents, and a positive and negative control. This kit can also have ALT2 specific antibodies (polyclonal or monoclonal). This kit includes a means for determining if a measurement of ALT1 and/or ALT2 indicates a diagnosis of damage or disease in ALT1 containing tissue and/or ALT2 containing tissue. The kit can also have instructions indicating when a level of ALT1 and/or ALT2 is indicative for diagnosis of damage or disease in tissue containing ALT1 or ALT2.

It is still another object of this invention to have a kit useful in determining when there are altered levels of ALT2 in bodily fluids (altered can be higher than normal or lower than normal). This kit can have a measurer of ALT2 levels in a bodily fluids sample and an indicator for determining if the ALT2 level measured falls in a range associated with a specific condition. It is a further object of this invention that the kit can determine when there are altered levels of ALT1 in bodily fluids (altered can be higher than normal or lower than normal). This kit can also have a measurer of ALT1 levels in a bodily fluids sample and another indicator for determining if the ALT1 level measured falls in a range associated with a specific condition. Furthermore, this kit can have a third indicator for comparing the values of ALT1 and ALT2 and determining if the levels of ALT1 and ALT2 fall in a range associated with a specific condition. The measurer of this kit can be selected from one or more of the following: a biologic assay, an antibody-based assay, an enzyme linked immunosorbent assay, a Western blot, a rapid immunoassay, a radioimmunoassay, and combinations thereof.

It is an object of this invention to have a method for producing a ALT polypeptide of the present invention. The ALT produced can be the same as the amino acid sequences of SEQ ID NO:1 or SEQ ID NO:2 or SEQ ID NO:5 or SEQ ID NO:6, or a homolog, fragment, or variant thereof. This method involves cloning the DNA encoding for ALT in an expression vector, introducing the expression vector into a host cell to produce a recombinant host cell, and subjecting to the recombinant host cell to conditions such that ALT is expressed. It is a further object of this invention that the ALT expressed can be isolated and purified. The DNA sequence placed in the plasmid can be the nucleic acid sequence of SEQ ID NO:3 or SEQ ID NO:4 or SEQ ID NO:7 or SEQ ID NO:8, or a nucleic acid sequence which encodes for a variant, homolog, or fragment of murine ALT1 or murine ALT2. Alternatively, the DNA sequence inserted into the plasmid may be a nucleic acid sequence which hybridizes, such as, for example, under conditions of high stringency, to a nucleic acid encoding a polypeptide of SEQ ID NO:1 or SEQ ID NO:2 or SEQ ID NO:5 or SEQ ID NO:6. In a specific embodiment, the high stringency conditions include 0.1×SSC with 0.1% SDS wash buffer at hybridization temperature, such as, for example, at about 60, 61, 62, 63, 64, 65, 66, 67, or 68 degrees C.

It is another object of this invention to have a method for diagnosing a condition associated by altered levels of ALT2 and/or ALT1 in bodily fluids in an animal, particularly a mouse and/or a rat. This method involves contacting a sample of bodily fluids with at least one antibody which specifically binds to an ALT2 of the present invention, detecting the ALT2 antibody which is bound to ALT2, and comparing the amount of detected ALT2 antibody to a known quantity for an animal without the condition. In this method when the quantity of detected ALT2 antibody differs sufficiently from the known quantity from an animal without the condition, then it indicates that the animal has the condition. In addition, the method also can involve contacting the sample of bodily fluids with at least one antibody which specifically binds to ALT1, detecting the ALT1 antibody which is bound to ALT1, and comparing said amount of detected ALT 1 antibody to a known quantity for an animal without the condition. In this method, when the quantity of detected ALT1 antibody differs sufficiently from the known quantity from an animal without the condition, then it indicates that the animal has the condition. Furthermore, this method can also involve comparing the amount of ALT2 antibody detected to the total amount of antibody detected and/or to the amount of ALT1 antibody detect; and/or the amount of ALT1 antibody detected to the total amount of antibody detected and/or to the amount of ALT2 antibody detected. Again, the condition is indicated if the amount of ALT2 antibody detected when compared to the amount of ALT 1 antibody detected or the total amount of antibody detected falls within a certain range.

Again, the condition is indicated if the amount of ALT1 antibody detected when compared to the amount of ALT2 antibody detected or the total amount of antibody detected falls within a certain range. It is a further object of this invention that the bodily fluids for this method can be selected from the following group: blood, serum, lymph, urine, sweat, mucus, sputum, saliva, semen, spinal fluid, interstitial fluid, synovial fluid, cerebrospinal fluid, gingival fluid, vaginal fluid, and pleural fluid.

One embodiment of the invention is an isolated and purified murine ALT polypeptide comprising the amino acid sequence selected from a group including SEQ ID NO:1 and SEQ ID NO: 2. Another embodiment of the invention is an isolated and purified polynucleotide encoding for the murine ALT polypeptide. The isolated and purified polynucleotide of one embodiment comprises a polynucleotide sequence selected from a group including SEQ ID NO:3 and SEQ ID NO:4. The invention also includes an isolated and purified antibody which binds specifically to the murine ALT polypeptides of the present invention. The invention further includes an expression vector for murine ALT comprising the murine ALT polynucleotide sequence operatively linked to an expression sequence.

Another embodiment of the invention is an isolated and purified rat ALT polypeptide comprising the amino acid sequence selected from a group including SEQ ID NO:5 and SEQ ID NO: 6. Another embodiment of the invention is an isolated and purified polynucleotide encoding for the rat ALT polypeptide. The isolated and purified polynucleotide of one embodiment comprises a polynucleotide sequence of SEQ ID NO:7 or SEQ ID NO:8. The invention also includes an isolated and purified antibody which binds specifically to the rat ALT polypeptides of the present invention. The invention further includes an expression vector for rat ALT comprising the rat ALT polynucleotide sequence operatively linked to an expression sequence.

Another embodiment of the invention is a method of detecting in a sample the presence of mRNA, wherein the mRNA encodes for an ALT polypeptide of the present invention. The method comprises contacting the sample with a polynucleotide probe, wherein the polynucleotide probe is sufficient to specifically detect under stringent hybridization conditions the presence of the mRNA, and detecting the formation of a hybrid of the polynucleotide probe and the mRNA.

Another embodiment of the invention is a method of detecting an ALT polypeptide of the present invention in a sample, wherein the sample comprises a bodily fluid, the method comprising contacting a sample of the bodily fluids with at least one antibody that specifically binds to the ALT polypeptide and detecting the antibody which is bound to the ALT polypeptide in the sample.

Yet another embodiment of the invention is a method of diagnosing or detecting injury or disease involving tissue which contains an ALT polypeptide of the present invention in an animal suspected of having the injury or disease. The method comprises: contacting a sample of bodily fluids from the animal with at least one first antibody, wherein the first antibody specifically binds to an ALT1 polypeptide; detecting the first antibody which is bound to the ALT1 polypeptide in the sample; contacting the sample of bodily fluids with at least one second antibody wherein the second antibody specifically binds to an ALT2 polypeptide; detecting the second antibody which is bound to the ALT2 polypeptide in the sample; and comparing the amount of the ALT1 polypeptide bound to the first antibody and the amount of the ALT2 polypeptide bound to the second antibody; wherein when the amount of the bound ALT2 polypeptide is sufficiently higher than the amount of the bound ALT1 polypeptide, it indicates that the animal has a disease or injury affecting tissue containing ALT2. The sample of bodily fluids can comprise a fluid selected from a group comprising blood, serum, lymph, urine, sweat, mucus, sputum, saliva, semen, spinal fluid, interstitial fluid, synovial fluid, cerebrospinal fluid, gingival fluid, vaginal fluid, and pleural fluid. The tissue can be selected from a group comprising liver, brain, muscle, adipose tissue, and kidney.

Another embodiment of the invention is a method of diagnosing or detecting injury or disease involving tissue which contains an ALT polypeptide in an animal suspected of having the injury or disease. The method comprises: contacting a sample of bodily fluids from the animal suspected of having the injury or disease with at least one first antibody wherein the first antibody specifically binds to an ALT polypeptide; detecting the first antibody which is bound to the ALT polypeptide in the sample; and comparing the amount of the ALT polypeptide in the sample of bodily fluids to an amount of ALT in the bodily fluids of an animal known not to have injury or disease involving tissue which contains ALT polypeptide; wherein when the amount of ALT in the bodily fluids of the sample is higher than the amount of ALT polypeptide in the bodily fluids of the animal known not to have injury or disease it indicates that the animal suspected has a disease or injury affecting tissue containing ALT. The sample of bodily fluids can comprise a fluid selected from a group including blood, serum, lymph, urine, sweat, mucus, sputum, saliva, semen, spinal fluid, interstitial fluid, synovial fluid, cerebrospinal fluid, gingival fluid, vaginal fluid, and pleural fluid. The tissue can be selected from a group comprising liver, brain, muscle, adipose tissue, and kidney.

A further embodiment of the invention is a diagnostic kit for use in diagnosing damage or disease in tissue containing an ALT polypeptide of the present invention. The kit comprises a measurer for determining a measurement of an ALT polypeptide in a sample of bodily fluids and an indicator for determining if the measurement falls in a range associated with damage or disease in the tissue containing the ALT of the present invention. In one embodiment, the ALT polypeptide is murine ALT2 of SEQ ID NO:2 or an amino acid sequence having about 95% homology thereto. In certain embodiments, the homolog is an amino acid sequence of SEQ ID NO:5. In another embodiment, the ALT polypeptide is rat ALT2 of SEQ ID NO:5 or an amino acid sequence having about 95% homology thereto. The measurer can be selected from a group comprising a biologic assay, an antibody-based assay, an enzyme linked immunosorbent assay, a Western blot, a rapid immunoassay, a radioimmunoassay, and combinations thereof.

Another embodiment of the invention is a diagnostic kit for use in diagnosing damage or disease in tissue containing an ALT polypeptide of the present invention. The kit comprises: an aliquot of antibodies that bind specifically to an ALT polypeptide of the present invention; immunoassay reagents; and a control for determining if a measurement of an ALT polypeptide of the present invention indicates a diagnosis of damage or disease in tissue containing an ALT polypeptide of the present invention. The control comprises instructions indicating that an increase or decrease in the amount of the ALT polypeptide indicates a diagnosis for damage or disease in tissue containing the ALT polypeptide. In a further embodiment, the kit further comprises an aliquot of antibodies that bind specifically to ALT2 polypeptides of the present invention and a control for determining if a measurement of said ALT2 polypeptide indicates a diagnosis of damage or disease in tissue containing said ALT2 polypeptide. The control comprises instructions indicating that an increase or decrease in the amount of ALT2 indicates a diagnosis for damage or disease in tissue containing the ALT polypeptide.

Another embodiment of the invention is a diagnostic kit for use in a condition associated with altered levels of an ALT polypeptide 1 in bodily fluids. The kit comprises a measurer for determining a measurement of an ALT 1 polypeptide in a sample of bodily fluids and an indicator for determining if the measurement falls in a range associated with the condition.

Another embodiment of the invention is a diagnostic kit for use in a condition associated with altered levels of an ALT 2 in bodily fluids. The kit comprises a measurer for determining a measurement of an ALT 2 polypeptide in a sample of bodily fluids and an indicator for determining if the measurement falls in a range associated with the condition.

Another embodiment of the invention is a diagnostic kit for use in a condition associated with altered levels of at least one of an ALT 1 and an ALT2 in bodily fluids. The kit comprises: a measurer for determining a first measurement of an ALT 1 polypeptide in a sample of bodily fluids; a measurer for determining a second measurement of ALT2 polypeptide in the sample of bodily fluids; and an indicator for determining if the first and second measurements fall in a range associated with the condition.

Still another embodiment of the invention is method of diagnosing a condition associated by altered levels of an ALT 1 in bodily fluids in an animal suspected of having the condition. The method comprises: contacting a sample of bodily fluids from the animal with at least one antibody wherein the antibody specifically binds to an ALT 1 polypeptide; detecting the antibody which is bound to the ALT 1 polypeptide in the sample; and comparing the amount of the detected antibody to a known quantity for an animal without the condition; wherein if the quantity of the detected antibody differs sufficiently from the known quantity from an animal without the condition, indicates that the animal has the condition.

Another embodiment of the invention is a method of diagnosing a condition associated by altered levels of an ALT 2 in bodily fluids in an animal suspected of having the condition. The method comprises: contacting a sample of bodily fluids from the animal with at least one antibody wherein the antibody specifically binds to an ALT 2 polypeptide; detecting the antibody which is bound to the ALT 2 polypeptide in the sample; and comparing the amount of the detected antibody to a known quantity for an animal without the condition; wherein if the quantity of the detected antibody differs sufficiently from the known quantity from an animal without the condition, indicates that the animal has the condition.

The sample of bodily fluids for the above methods and/or kits can comprise a fluid selected from a group comprising of blood, serum, lymph, urine, sweat, mucus, sputum, saliva, semen, spinal fluid, interstitial fluid, synovial fluid, cerebrospinal fluid, gingival fluid, vaginal fluid, and pleural fluid.

The measurer for above methods and/or kits can be selected from the group comprising a biologic assay, an antibody-based assay, an enzyme linked immunosorbent assay, a Western blot, a rapid immunoassay, a radioimmunoassay, and combinations thereof.

Another embodiment of the invention is a method of producing an ALT polypeptide. The method comprises: providing an ALT polynucleotide sequence in an expression vector; introducing the expression vector into a host cell such that a recombinant host cell is produced; and subjecting to the recombinant host cell to conditions such that the ALT polypeptide is expressed. In one embodiment, the ALT polynucleotide sequence is selected from a group including SEQ ID NO:3 and SEQ ID NO:4. In another embodiment, the ALT polynucleotide sequence is selected from a group including SEQ ID NO:7 and SEQ ID NO:8.

BRIEF DESCRIPTION OF THE DRAWINGS

FIGS. 1A-B are a comparison of the sequence of murine ALT isoenzymes (mALT1 and mALT2) of this invention and the polypeptide sequence of human ALT isoenzymes. FIG. 1A is a comparison between SEQ ID NO:1 (murine ALT1) and human ALT1. FIG. 1B is a comparison between SEQ ID NO:2 (murine ALT2) and human ALT2. Peptide sequences are aligned using BESFIT from the GCG package and amino acids are numbered to the right of the sequence. Identical amino acids are denoted by a vertical bar, strongly similar amino acids by a colon (:), and weakly similar amino acids by a period (.).

FIGS. 4A and 4B are Northern blots of total RNA extracted from fatty liver of obese (ob/ob) and lean (+/?) mice blotted with $^{32}$P-labeled mALT1 or mALT2 DNA probe. FIG. 4C is a graph of murine ALT expression.

FIG. 6 is a sequence alignment of ALT1 and ALT2 polypeptides from human, mouse (SEQ ID NO:1 and SEQ ID NO:2) and rat species (SEQ ID NO:6 and SEQ ID NO:5). Highly conserved amino acids (≧90%) are in capital letters and less conserved (<90% and ≧50%) are in small letters. Symbol "!" is for any amino acids of I or V, "$" for L or M, "%" for F or Y, and "#" is for N, D, Q, E, B, or Z.

DEFINITIONS

Figure 2:
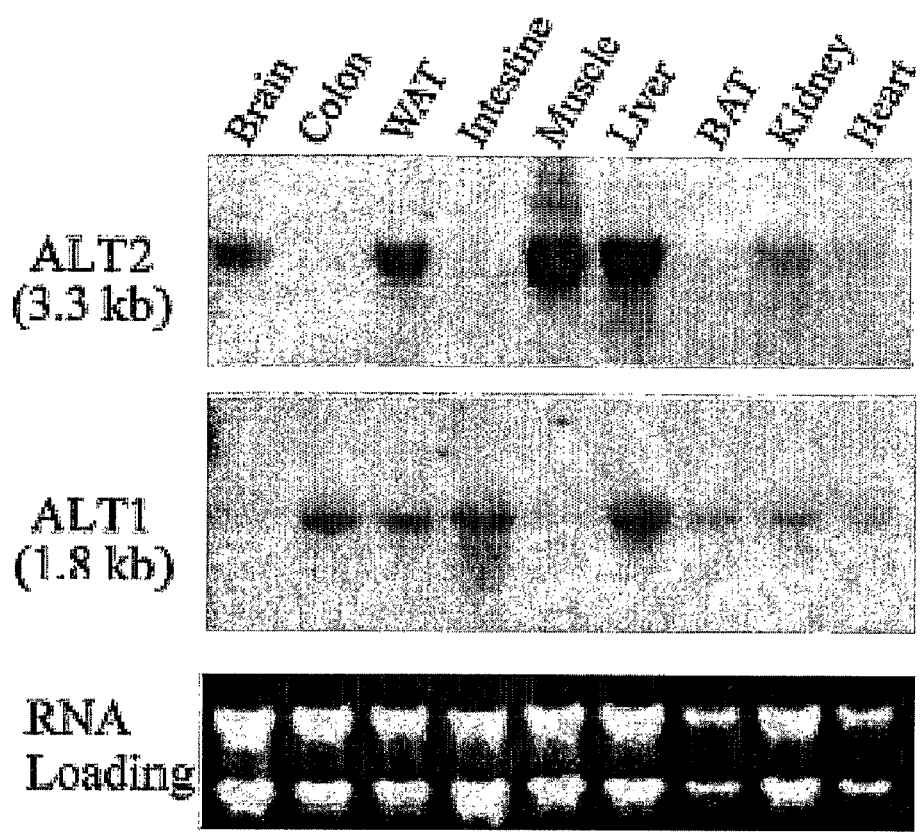
FIG. 2 is Northern blots showing the expression of murine ALT mRNA. Blots from duplicate gels containing pooled total RNAs (15 µg/lane) from 3 to 4 mice were probed separately with $^{32}$P-labeled murine ALT1 or ALT2 cDNAs. Hybridization signals were visualized by autoradiography. RNA loading from one of the duplicate gels is shown in the lower blot. The size of the mRNA transcripts is indicated in parentheses.

Within the context of this specification, each term or phrase below will include the following meaning or meanings.

The terms "murine ALT polypeptide," "murine ALT protein," "murine ALT," and "mALT" are interchangeable and generally refer to or include any and/or all murine ALT polypeptides or isoenzymes, including murine ALT1, murine ALT2, and any variant, homolog, or fragment of murine ALT1 or murine ALT2.

The terms "rat ALT polypeptide," "rat ALT protein," "rat ALT," and "rALT" are interchangeable and generally refer to or include any and/or all rat (rattus) ALT polypeptides or isoenzymes, including rat ALT1, rat ALT2, and any variant, homolog, or fragment of rat ALT1 or rat ALT2.

The terms "protein" and "polypeptide" are used interchangeably in both singular and plural forms, as are the terms "nucleic acid" and "polynucleotide."

These and additional terms may be defined with additional language in the remaining portions of the specification.

DETAILED DESCRIPTION OF THE PRESENTLY PREFERRED EMBODIMENTS

The present invention covers the nucleotide and amino acid sequences of murine ALT, antibodies specific to murine ALT, and the use of these polypeptides, polynucleotides, and antibodies to diagnose various diseases and conditions in tissue that produce murine ALT, such as fatty liver, and to differentially diagnose liver injury caused by fatty liver (liver steatosis) and by alcohol, trauma, infection, toxicity, and other causes of liver damage.

This invention also includes homologs and functional fragments of murine ALT polypeptides as well as expression vectors containing murine ALT polynucleotide sequences and recombinant host cells which contain an expression vector containing murine ALT polynucleotide sequences.

This invention also includes homologs and functional fragments of rat ALT polypeptides as well as expression vectors containing rat ALT polynucleotide sequences and recombinant host cells which contain an expression vector containing rat ALT polynucleotide sequences.

For this application, homology is often measured using sequence analysis software (e.g., Sequence Analysis Software Package of the Genetics Computer Group, University of Wisconsin Biotechnology Center, 1710 University Avenue, Madison, Wis. 53705 or the NCBI BLAST program). Such software matches similar sequences by assigning degrees of homology to various substitutions, deletions, substitutions, and other modifications.

The term "functional fragments" include those fragments of SEQ ID NO:1 and/or SEQ ID NO:2 and/or SEQ ID NO:5 and/or SEQ ID NO:6 and/or a polypeptide having about 95% sequence identity to that of the SEQ ID NO:1 and/or SEQ ID NO:2 and/or SEQ ID NO:5 and/or SEQ ID NO:6 and that retains the function, activity, or immunobiological properties of said ALT polypeptide. One of skill in the art can screen for the functionality of a fragment by using the examples provided herein, where full length ALT1 and ALT2 are described. By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed (e.g., as described herein). Preferably, such a sequence is at least 85%, and more preferably from 90%, 91%, 92%, 93%, 94%, 95%, 96%, 97%, 98%, 99%, to 100% homologous at the amino acid level to SEQ ID NO:1 or SEQ ID NO:2 or SEQ ID NO:5 or SEQ ID NO:6.

Functional Equivalence

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the RNA sequence, according to the following codon table:

TABLE 1

| Amino Acids | Codons |
|---|---|
| Alanine | Ala A GCA GCC GCG GCU |
| Cysteine | Cys C UGC UGU |
| Aspartic acid | Asp D GAG GAU |
| Glutamic acid | Glu E GAA GAG |
| Phenylalanine | Phe F UUC UUU |
| Glycine | Gly G GGA GGC GGG GGU |
| Histidine | His H CAC CAU |
| Isoleucine | Ile I AUA AUC AUU |
| Lysine | Lys K AAA AAG |
| Leucine | Leu L UUA UUG CUA CUC CUG CUU |
| Methionine | Met M AUG |
| Asparagine | Asn N AAC AAU |
| Proline | Pro P CCA CCC CCG CCU |
| Glutamine | Gln Q CAA CAG |
| Arginine | Arg R AGA AGG CGA CGC CGG CGU |
| Serine | Ser S AGC AGU UCA UCC UCG UCU |
| Threonine | Thr T ACA ACC ACG ACU |
| Valine | Val V GUA GUC GUG GUU |
| Tryptophan | Trp W UGG |
| Tyrosine | Tyr Y UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and messenger RNA sequence, and nevertheless obtain a protein with like properties. It is thus contemplated by the inventors that various changes may be made in the peptide sequences of the disclosed compositions, or corresponding DNA or RNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within .+−.2 is preferred, those which are within .+−.1 are particularly preferred, and those within .+−0.05 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within .+−.2 is preferred, those which are within .+−.1 are particularly preferred, and those within .+−.0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

It will also be understood that amino acid sequences may include additional residues, such as additional N- or C-terminal amino acids and yet still be essentially as set forth in one of the sequences disclosed herein, so long as the sequence meets the criteria set forth above, including the maintenance of biological protein activity where protein expression is concerned. The addition of terminal sequences particularly applies to sequences, which may, for example, include various unnaturally occurring amino acid sequences flanking either of the N- or C-termini to allow for facile covalent linkage to another molecule, i.e., a reporter molecule.

In non-limiting examples, the homolog may include a substitution in SEQ ID NO:1 of C56R, F109L, D126N, R133K, I152V, P158L, Q165R, A200S, R204H, A05T, A222T, D227G, R249H, C253G, R258H, V263A, E291K, G293R, M297L, A328S(*), V339T, E352A, M387L, T393A, S395T, K400A, R406K, E408A, R421S, Q434R, L439P, K440R, Q443E, D447E(*), C459R, Q477R, M491L, V496L(*), R502S(*), H503R, H510L or a combination thereof.

In a non-limiting example, the homolog may include a substitution in SEQ ID NO:6 of C56R, F109L, D126N, R133K, I152V, P158L, Q165R, S200A, R204H, A205T, A222T, D227G, R249H, C253G, R258H, V263A, K291E, G293R, M297L, S328A, V339T, E352A, M387L, T393A, S395T, K400A, R406K, E408A, R421S, Q434R, L439P, K440R, Q443E, E447D, C459R, Q477R, M491L, L496V, S502R, H503R, H510L or a combination thereof.

In a non-limiting example, the homolog may include a substitution in SEQ ID NO:5 of H24Q, D45E, M77L, H99Q, N123D, L196I, I228V, D245N, L251V, R252Q, Q253E, Q321E, P326H, V392E, S407F, Q430H, L445F, S456A, K458Q, E501D, H508Q, L515I, K516N, K520Q, S522A or a combination thereof.

In a non-limiting example, the homolog may include a substitution in SEQ ID NO:2 of H24Q, D45E, M77L, H99Q, N123D, L196I, V228I, D245N, L251V, R252Q, Q253E, Q321E, H326P, E392V, F407S, Q430H, L445F, S456A, K458Q, D501E, H508Q, L515I, K516N, Q520K, S522A or a combination thereof.

By a "substantially pure polypeptide" is meant a ALT polypeptide that has been separated from components that naturally accompany it. Typically, the polypeptide is substantially pure when it is at least 60%, by weight, free from the proteins and other naturally occurring molecules with which it is typically associated. Preferably, the preparation is at least 75%, 80%, 90%, 95%, and most preferably at least 99%, by weight, an ALT polypeptide. A substantially pure ALT polypeptide can be obtained, for example, by extraction from a natural source; by expression of a recombinant nucleic acid encoding the desired ALT polypeptide; or by chemically synthesizing the protein. Purity can be measured by any appropriate method, e.g., column chromatography, polyacrylamide gel electrophoresis, or by HPLC analysis.

A protein is substantially free of naturally associated components when it is separated from those contaminants that accompany it in its natural state. Thus, a protein that is chemically synthesized or produced in a cellular system different from the cell from which it naturally originates is substantially free from its naturally associated components. Accordingly, substantially pure polypeptides include those derived from eukaryotic organisms but synthesized in *E. coli* or other prokaryotes. As will be appreciated by one skilled in the art following the teachings herein provided, the polynucleotide molecules of the present disclosure can be expressed in a variety of prokaryotic and eukaryotic cells using regulatory sequences, vectors, and methods well established in the literature.

An ALT polypeptide produced according to the present description can be purified using a number of established methods such as affinity chromatography using anti-mALT antibodies coupled to a solid support. Fusion proteins of an antigenic tag and an ALT polypeptide can be purified using antibodies to the tag. Optionally, additional purification is achieved using conventional purification means such as liquid chromatography, gradient centrifugation, and gel electrophoresis, among others. Methods of protein purification are known in the art and can be applied to the purification of recombinant ALT polypeptide described herein.

Construction of ALT encoded fusion proteins is also contemplated. Fusion proteins typically contain additions, substitutions, or replacements of one or more contiguous amino acids of the native ALT polypeptide with amino acid(s) from a suitable fusion protein partner. Such fusion proteins are obtained using recombinant DNA techniques generally well known by one of skill in the art. Briefly, DNA molecules encoding the hybrid ALT protein of interest are prepared using generally available methods such as PCR mutagenesis, site directed mutagenesis, and/or restriction digestion and ligation. The hybrid DNA is then inserted into expression vectors and introduced into suitable host cells.

Recombinant gene expression vectors comprising a nucleic acid encoding an ALT protein of interest, or portions thereof, can be constructed in a variety of forms well-known in the art. Preferred expression vectors include plasmids and cosmids. Expression vectors include one or more fragments of murine ALT. In one embodiment of this invention, an expression vector comprises a nucleic acid encoding an ALT polynucleotide sequence of SEQ ID NO:1 or SEQ ID NO:2 or SEQ ID NO:5 or SEQ ID NO:6. As used herein, the phrase "operatively encode" refers to one or more protein coding regions associated with those regulatory sequences required for expression of the polypeptide encoded by the coding region. Examples of such regulatory regions including promoter binding sites, enhancer elements, ribosome binding sites, and the like. Those of ordinary skill in the art following the teachings herein provided will be able to select regulatory sequences and incorporate them into the recombinant expression vectors described herein without undue experimentation. For example, suitable regulatory sequences for use in various eukaryotic and prokaryotic systems are described in Ausubel, et al., *Short Protocols in Molecular Biology*, 3rd ed., John Wiley & Sons, Inc, New York, 1997, which is hereby incorporated by reference in its entirety.

Expression vectors for use with ALT typically contain regulatory sequences derived from a compatible species for expression in the desired host cell. For example, when *E. coli* is the host cell, the host cell population can be typically transformed using pBR322, a plasmid derived from an *E. coli* species. (Bolivar, et al., Gene, 2: 95, 1977). pBR322 contains genes for ampicillin (AMPR) and tetracycline resistance and thus provides easy means for identifying transformed cells.

Promoters suitable for use with prokaryotic hosts illustratively include the betalactamase and lactose promoter systems (Chang, et al., Nature, 275: 615, 1978; and Goeddel, et al., Nature, 281: 544, 1979), alkaline phosphatase, the tryptophan (trp) promoter system (Goeddel, Nucleic Acids Res., 8: 4057, 1980) and hybrid promoters such as the taq promoter (de Boer, et al., Proc. Natl. Acad. Sci. USA, 80: 21-25, 1983). Other functional bacterial promoters are also suitable. Their nucleotide sequences are generally known in the art, thereby enabling a skilled worker to ligate them to a polynucleotide which encodes the peptide of interest (Siebenlist, et al., Cell, 20: 269, 1980) using linkers or adapters to supply any required restriction sites.

In addition to prokaryotes, eukaryotic microbes such as yeast cultures can also be used as source for the regulatory sequences. *Saccharomyces cerevisiae* is a commonly used eukaryotic host microorganism. Suitable promoting sequences for use with yeast hosts include the promoters for 3-phosphoglycerate kinase (Hitzeman, et al., J. Biol. Chem., 255: 2073, 1980) or other glycolytic enzymes (Hess, et al. J. Adv. Enzyme Reg. 7: 149, 1968; and Holland, Biochemistry, 17: 4900, 1978) such as enolase, glyceraldehyde-3-phosphate dehydrogenase, hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degraded enzymes associated with nitrogen metabolism, metallothionine, glyceraldehyde-3-phosphate dehydrogenase, and enzymes responsible for maltose and galactose utilization. Yeast enhancers also are advantageously used with yeast promoters.

In another embodiment, a recombinant virus is used as the expression vector. Exemplary viruses include the adenoviruses, adeno-associated viruses, herpes viruses, vaccinia, or an RNA virus such as a retrovirus or an alphavirus. Preferably, the retroviral vector is a derivative of a murine or avian retrovirus. Preferably the alphavirus vector is derived from Sindbis or Semliki Forest Virus. All of these vectors can transfer or incorporate a gene for a selectable marker so that transduced cells can be identified and generated.

By inserting one or more sequences of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector, such as to the vicinity of a mucosal inductor site, using, for example, a mALT-specific antibody. Those of skill in the art know of, or can readily ascertain without undue experimentation, specific polynucleotide sequences which can be inserted into the retroviral genome to allow target specific delivery of the retroviral vector containing the polynucleotides of interest.

Construction of suitable vectors containing desired coding, non-coding and control sequences employ standard ligation techniques. Isolated plasmids or DNA fragments are cleaved, tailored, and re-ligated in the form desired to construct the plasmids required.

For example, for analysis to confirm correct sequences in plasmids constructed, the ligation mixtures can be used to transform a host cell and successful transformants selected by antibiotic resistance where appropriate. Plasmids from the transformants are prepared, analyzed by restriction and/or sequenced by, for example, the method of Messing, et al., (Nucleic Acids Res., 9: 309, 1981), the method of Maxam, et al., (Methods in Enzymology, 65: 499, 1980), or other suitable methods which are known to those skilled in the art. Size separation of cleaved fragments is performed using conventional gel electrophoresis as described, for example, by Maniatis, et al., (Molecular Cloning, pp. 133-134, 1982).

Host cells can be transformed with the expression vectors described herein and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan following the teachings herein provided.

Figures 1A, 1B:
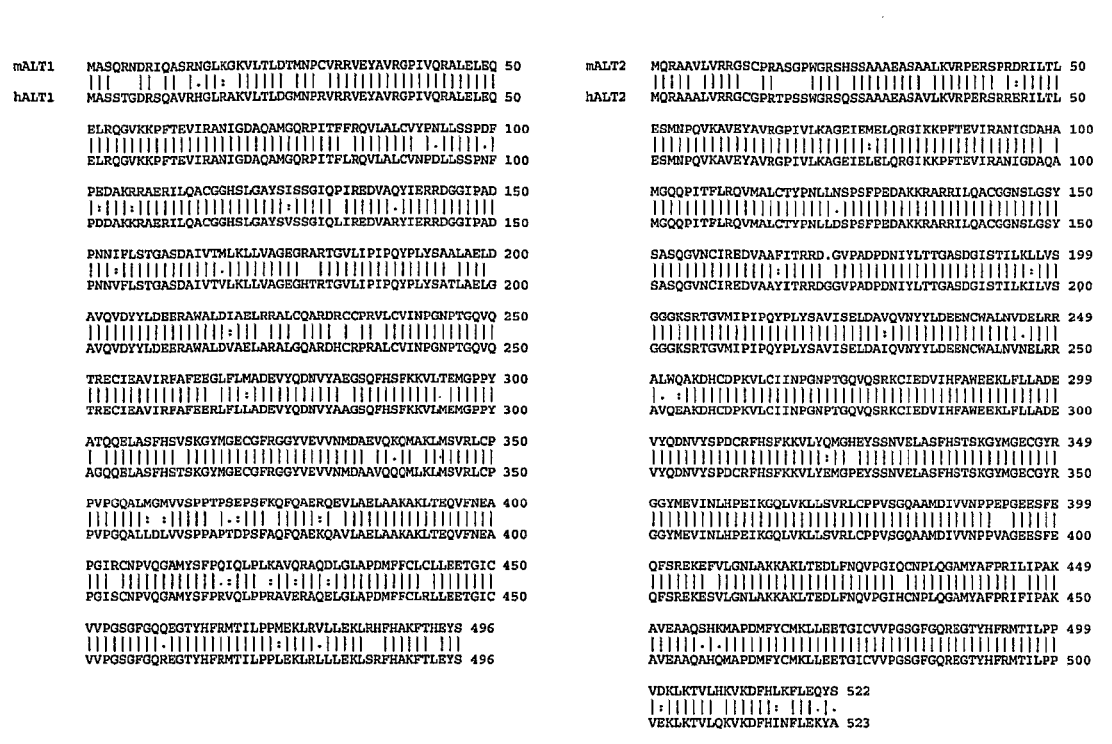

In cloning murine ALT1 and murine ALT2, peptide sequences of human ALT1 and ALT2 were used as probes to search the mouse murine expressed sequence tag (EST) database using tBLASTn. A search of the mouse EST database using human ALT1 and human ALT2 peptide sequences as probes yielded several highly homologous EST clones. Of them, IMAGE clones 4195300 and 5065322 were fully sequenced and revealed the highest homology to human ALT1 and ALT2, respectively, in the entire protein-coding region. The DNA nucleotide sequences of these two clones were confirmed by sequencing analysis and are predicted to encode proteins of 496 (clone 4195300) and 522 (clone 5065322) amino acids. As shown in FIG. 1, comparison of the mouse and human peptide sequences revealed that IMAGE clone 4195300 shares about 87% identity and about 89% similarity to human ALT1, but about 70% identity and about 72% similarity to human ALT2, whereas clone 5065322 shares about 93% identity and about 95% similarity with human ALT2, but about 69% identity to human ALT1. The cDNA clone 4195300 and the clone 5065322 were thus determined to be murine ALT1 and murine ALT2, respectively. Sixty-seven percent of amino acids are identical in murine ALT1 and murine ALT2; a similar degree of conservation, about 68%, is found between human ALT1 and ALT2.

Cloning of rat ALT1 and ALT2 was achieved through bioinformatics by interrogating the closest homolog in GenBank with murine and human ALT1 and ALT2 protein sequences. The rat IMAGE clone 7113147 encodes a protein that shares 95% and 98% identity to human and murine ALT2, respectively, but 68% and 67% identity to human and murine ALT1, respectively. Thus, the cDNA clone 7113147 was determined as rat ALT2. Rat ALT1 cDNA was cloned from rat liver first-strand cDNA by PCR amplification with high-fidelity DNA polymerase using primers based rat expressed sequence tags (ESTs) which shares highest identity to murine and human ALT1 sequences. The resultant PCR fragment was cloned into TOPO cloning vector (Invitrogen) and sequenced in full. The translated protein sequence shares high identities of 88% and 97% to human and murine ALT1, respectively, but low identities of 70% and 68% to human and murine ALT2, respectively. Thus, this clone was determined as rat ALT1.

The gene expression of murine ALT1 and murine ALT2 was examined in mouse tissues by Northern analysis. Male obese mice (ob/ob), littermate control (+/?), and C57BL/6J, 6 to 8 weeks old, were obtained from Jackson Laboratory and euthanized with $CO_2$ according to protocol approved by Institutional Animal Care and Use Committee. Tissues were immediately frozen in liquid nitrogen until use for RNA extraction or enzyme activity assay. Total RNA was prepared with Trizol, available from Life Technologies Inc., Gaithersburg, Md., from the snap-frozen tissues. For the tissue distribution study, pooled 15 µg of total RNA from 3 to 4 mice were electrophoresed on a 1.2% agarose gel and blotted to a Nitroplus membrane, available from Schleicher & Schuell, Dassel, Germany. The DNA probes of murine ALT1 (1.4 kb) and murine ALT2 (2.4 kb) were derived from restriction enzyme digestion of IMAGE clone 4195300 (Sal I/Not I) and clone 5065322 (Sal I/Not I), respectively. Probes were random-labeled with $^{32}$P-dCTP, hybridization was carried out at 65° C. in Rapid-hyb buffer, available from Amersham Biosciences, Piscataway, N.J., and blots were washed twice with 0.5×SSC/1% SDS at 65° C. (stringent wash) and visualized by PhosphorImager, available from Amersham Biosciences, or x-ray film.

As shown in FIG. 2, the ≈3.3 kb murine ALT2 messenger RNA (mRNA) was expressed at high levels in muscle, liver, and white adipose tissue (WAT), at moderate levels in brain and kidney, and at a low level in heart. By contrast, the ≈1.8 kb murine ALT1 mRNA was highly expressed in liver and considerably in WAT, intestine, and colon tissue. As shown in FIG. 2 particular tissues selectively express one ALT isoenzyme over the other. For instance, murine ALT2 was significantly expressed, and murine ALT1 barely expressed, in muscle and brain tissue. In contrast, bowel tissue generally expressed only murine ALT1, and not murine ALT2.

To determine the chromosomal localization of DNA encoding murine ALT1 and murine ALT2 (gpt1 and gpt2), the corresponding cDNAs were searched against the mouse genome and localized gpt1 to murine chromosome 15D3 and gpt2 to chromosome 8C2. Both of these regions are syntenic to the chromosomal regions where human gpt1 (chromosome 8q24.3) and gpt2 (chromosome 16q12.2) reside. Full-length cDNAs of mALT1 (BC022625) and mALT2 (BC34219) were searched against the mouse genome sequence database with BLASTn, and their chromosomal localizations were determined by MapViewer.

The coding region of mALT1 cDNA was amplified by polymerase chain reaction (PCR) at 28 cycles at 94° C. for 30 seconds, 56° C. for 30 seconds, and 72° C. for 1.5 minutes, with a final extension of 7 minutes at 72° C. using the Turbo Pfu PCR system (Stratagene) with an NdeI-linked primer, p1408 5'-GGAAGATCTCATATGGCCTCACAAAG-GAATGAC-3' (nt<106-126, BC022625; SEQ ID NO:9), and a NotI;-linked primer, p1409 5'-AATGCGGCCGCTCAG-GAGTACTCATGAGTGAA-3' (1596-1576, BC022625; SEQ ID NO:10), using IMAGE clone 4195300 as a template. The resulting PCR product was digested with NdeI/NotI and subcloned into pET28a, available from Novagen, Madison, Wis., creating plasmid pET28-mALT1. The absence of mutations in the inserted murine ALT1 cDNA was verified by DNA sequence analysis. The same approach was used to clone the coding region of murine ALT2 cDNA from IMAGE clone 5065322 into pET28a by PCR using IMAGE clone 5065322 as template with primer p1405 5'-GGAAGATCTC-CATGGCCCATATGCAGCGGGCAGCGGTGCTGGT-3' (nt 128-150, BC034219; SEQ ID NO:11) and p1406 5'-AAT-GCGGCCGCTCATGAGTACTGCTCCAGGAA-3' (nt 1696-1676, BC034219; SEQ ID NO:12), creating plasmid pET28-mALT2.

To express mALT1 and mALT2 proteins, plasmid pET28-mALT1, pET28-mALT2, or empty vector pET28 were used to transform competent E. coli. (Tuner DE3, available from Novagen). A fresh colony of the transformants was grown in 50 ml LB media containing 30 μg/ml kanamycin to an $OD_{600}$ of 0.7, at which time isopropyl-beta-D-thiogalactopyranoside (IPTG) was added (1 mmol, final concentration) to induce expression of the recombinant proteins. Cell pellets were harvested from 20 ml cultures before and after 4 hours of induction and were resuspended in 5 ml of TE buffer (10 mmol Tris-HCl (pH 7.4), 0.1 mmol ethylenediaminetetraacetic acid), followed by a brief sonication, 3×10 seconds, setting 3 using a Fisher 550 Sonic Dismembrator. Cell lysates were centrifuged at 10,000 g for 15 minutes at 4° C., and supernatants were analyzed immediately for enzyme activity and protein analysis.

Figure 3A:
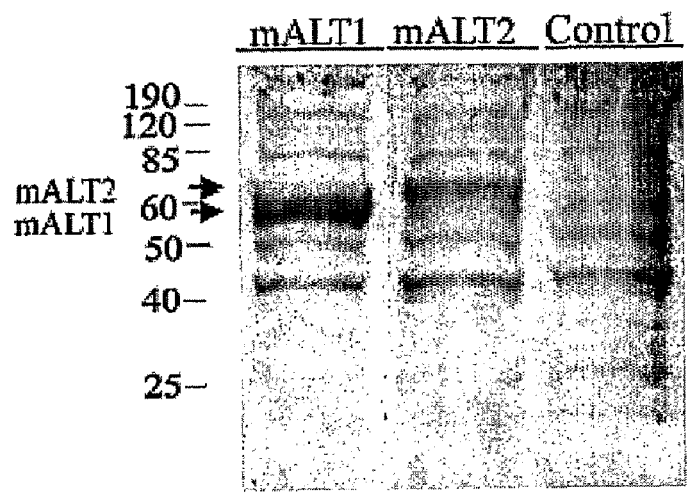
FIG. 3A is an electrophoresis gel where thirty microliters of E. coli extracts containing 100 to 150 µg of protein were analyzed on 4%-20% SDS-PAGE and stained with Coomassie Blue. Arrows indicate IPTG induced protein bands corresponding to mALT1 and mALT2.
Figure 3B:
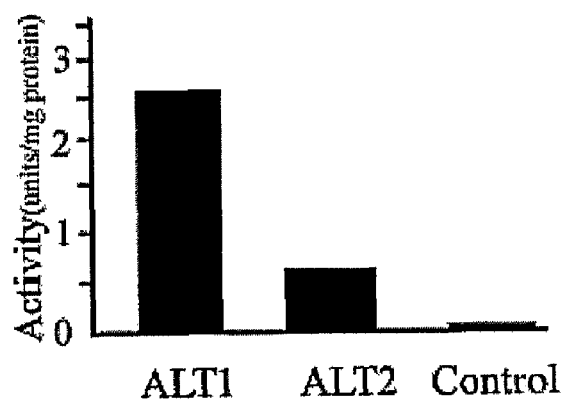
FIG. 3B is a graph of ALT activity of soluble cell extracts of E. coli harboring plasmid pET28-mALT1 (ALT1), pET28-mALT2 (ALT2), or empty vector pET28 (control) after IPTG induction.

Soluble fractions of cell lysates were assayed for ALT activity and subjected to sodium dodecyl sulfate-polyacrylamide gel electrophoresis (SDS-PAGE) analysis. As shown in FIG. 3A, under induction of IPTG, significant ALT activity was observed in cell lysates from bacteria transformed with pET28-mALT1 (2.62 units/mg protein) and pET28-mALT2 (0.72 units/mg protein), compared to empty vector control (0.19 units/mg protein). Accordingly, as shown in FIG. 3B, protein bands at approximate molecular weights (MW) of 58 kd and 62 kd were clearly visible in bacterial cell pellets after IPTG induction, corresponding to murine ALT1 (calculated MW=55 kd) and murine ALT2 (calculated MW=58 kd). It should be noted that murine ALT activities detected in the above cell lysates do not reflect the specific activity of the murine ALT isoenzymes, as most of the recombinant proteins were expressed in insoluble fraction of inclusion body, and, therefore, the actual amount of ALT in the cell lysates was not known. Nevertheless, these data confirm that murine ALT1 and ALT2 cDNAs encode functional murine ALT.

The ALT activity of the bacterially expressed recombinant murine ALT proteins was confirmed using a GPT Optimized Alanine Aminotransferase kit, available from Sigma Diagnostics (catalog no. DG159-K), St. Louis, Mo., according to manufacturer instructions. Briefly, 0.5 ml of cell lysate was incubated with a 2.5 ml mixture of reagent A and B containing L-alanine, nicotinamide adenine dinucleotide, Lactate Dehydrogenase, and 2-oxoglutarate at 25° C. Absorbance at 340 nm was recorded at 1, 2, and 3 minutes after incubation. The slope of absorbance decrease is proportional to ALT activity. Protein concentration of cell lysates were determined by Coomassie Brilliant Blue G250 (BioRad) using bovine serum albumin as a standard. Final ALT activities were corrected by protein concentration of cell lysates. One unit of ALT activity was defined as the amount of enzyme that catalyzes the formation of 1 μmol/liter of nicotinamide adenine dinucleotide per minute at 25° C.

To demonstrate hepatic ALT and aspartate aminotransferase (AST) activity, a piece of snap-frozen liver (50-60 mg) was thawed on ice and then minced and homogenized in 19 volumes of TE buffer (wt/vol) with Dounce homogenizer (40 times). The resulting homogenate was further sonicated (3×10 seconds, setting 4, using a Fisher 550 Sonic Dismembrator) followed by centrifugation at 10,000 rpm for 15 minutes at 4° C. The supernatant was assayed for hepatic ALT using an L-type GPT J2 kit, available from Wako Chemicals, Osaka, Japan, according to the manufacturer's instructions. AST activity was measured with an AST/GOT Liqui-UV kit, available from Stanbio Laboratories, Boerne, Tex., according to the manufacturer's instructions.

Figure 5:
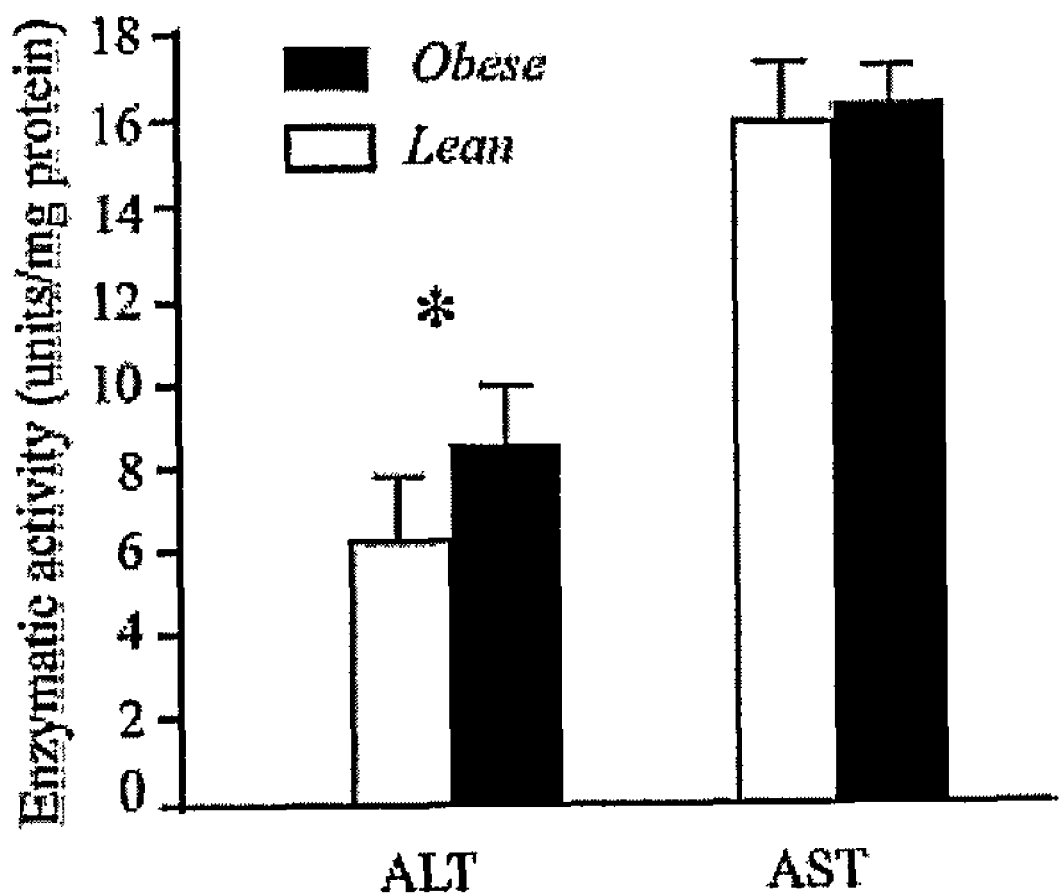
FIG. 5 is a graph of ALT and AST activities in obese (ob/ob) and lean (+/?) mice measured for their ALT and AST activities. Activities are expressed as mean±SD (n=7). *P<0.05 is considered statistically significant.

Murine ALT2 gene expression is specifically induced in fatty liver. The distinctive tissue distribution patterns of murine ALT1 and ALT2 mRNAs are likely due to a difference in their gene regulation. Gene expression differences were examined in fatty livers of obese mice (ob/ob). FIGS. 4A-C demonstrate the increased mALT2 gene expression in fatty liver. FIGS. 4A and 4B are duplicate blots containing 15 μg of total RNA extracted from fatty liver of obese (ob/ob) and lean (+/?) mice blotted with $^{32}$P labeled mALT1 or mALT2 DNA probe. Hybridization signals were visualized and quantitated by PhosphorImager. In FIGS. 4A and 4B, RNA loading from one of the duplicate gels is shown in lower blot. FIG. 4C shows data expressed as mean±SD (n=3). *P<0.05 is considered statistically significant. As shown in FIGS. 4A-C, compared to the normal liver of the lean mice control (+/?), the expression of murine ALT2 mRNA was elevated about 1-fold, but that of murine ALT1 remained unchanged. Furthermore, a significant elevation (30%, P<0.01) of murine ALT enzymatic activity was observed in fatty liver relative to normal liver. The data indicates that murine ALT2 induction is most generally responsible for the increased murine ALT activity in fatty liver. Interestingly, as shown in FIG. 5, AST activity was barely increased in fatty liver (5%, P=0.5) compared with normal liver.

Thus the invention provides molecular cloning of animal homologues of human ALT1 and ALT2. ALT is an important intermediary enzyme involved in the metabolism of amino acids, glucose, and possibly fatty acids and is well known for its use as a surrogate marker for liver damage in clinical diagnostics. In addition to the dissimilarity of the peptide sequences of murine ALT1 and murine ALT2, the mouse genes reside on separate chromosomes and have distinct tissue distributions and possibly cellular localizations. The murine ALT isoenzymes behave discordantly in various clinical conditions. In other words, under certain clinical conditions, one isoenzyme may be elevated but not the other, or vice versa. By virtue of this feature, individual murine ALT isoenzymes can be better diagnostic markers than a total murine ALT activity. Similarly, individual rat ALT isoenzymes can be better diagnostic markers than a total rat ALT activity.

ALT activities are present in many tissues, including liver, heart, kidney, muscle, brain, and adipose tissue in rodents. Northern blot data indicate one or both of the murine ALT genes are expressed in the tissues where ALT activity has been observed. Murine ALT1 is mainly expressed in liver and bowels, whereas murine ALT2 is highly expressed in muscle, liver, fat, and kidney, a tissue pattern reminiscent of human ALT1 and ALT2 tissue distribution. The conservation among rat, murine and human ALT isoenzymes in protein sequence, gene localization, and tissue distribution forms a basis for using the rat and/or mouse as a model for exploring the diagnostic value of ALT isoenzymes.

ALT and AST activity levels have been used in clinic diagnostics for many years. Elevation of these two enzyme activities in serum are regarded as evidence of liver damage, as in viral hepatitis, NASH, or drug hepatotoxicity. However, the mechanism for the serum ALT increase has not been well understood and has been thought to be caused by "leakage" of the cellular enzyme into the systemic circulation. Moreover, which ALT isoenzyme is responsible for the serum elevation has not been known because the current ALT assay measures total catalytic activity of ALT, presumably the combined activity of ALT1 and ALT2.

Molecular cloning of ALT isoenzymes in rat and mice provides a means to study the underlying mechanism(s) as well as an interpretation of clinical ALT observations. For example, ALT elevation in muscle disease may be due to a "leak" of ALT, presumably ALT2, from muscle, where ALT2, but not ALT1, is abundantly expressed. Similarly, a specific ALT isoenzyme may be induced in a given clinical condition.

The hepatic murine ALT1 and murine ALT2 gene expression were examined in obese mice because hepatic steatosis is associated with this genetically obese model. Indeed, murine ALT2, but not murine ALT1, gene expression is specifically induced. Furthermore, total murine ALT enzymatic activity is increased by 30% in fatty liver over nonfatty liver, suggesting that murine ALT2 may be primarily responsible for the increased serum ALT activity in liver steatosis. Interestingly, AST activity remains unchanged in the same condition. These animal findings are in agreement with clinical observations in which serum ALT is generally increased to a greater extent than AST in patients with liver steatosis.

Additionally, the ALT isoenzymes may be present in different cellular compartments, which can also be utilized for diagnostic purposes: the release of a given ALT isoenzyme into circulation reflects the nature of the liver damage. It has been shown that serum mitochondrial AST content is specifically increased in patients treated with halothane, and suggested that this AST isoenzyme is a sensitive marker for halothane-induced hepatic injury. Both cytosolic and mitochondrial murine and rat ALT activities were found in liver, kidney, and skeletal and cardiac muscles. At present, which ALT isoenzyme is cytosolic or mitochondrial is not certainly clear. ALT isoenzyme specific antibodies help to elucidate the cellular localization of ALT isoenzymes and their changes in disease states.

In certain embodiments of the present invention, ALT isoform-specific antibody is required for establishment of isoform-specific detection, such as by enzyme-linked immunoabsorbant assay (ELISA). For this purpose, a recombinant ALT1 polypeptide and/or a recombinant ALT2 polypeptide is generated in bacteria and purified to homogeniety. About 2 mg of the purified protein is used to immunize mice for generating antibody specific for murine ALT or, alternatively, to immunize rats for generating antibody specific for rat ALT. As a result, a monoclonal hybridoma against a isoform of an ALT polypeptide of the present invention is determined by determining binding specificity to said ALT polypeptide. One such method is Western blot analysis in which about 20 ng of ALT2, of ALT1, and of bovine serum albumin are load onto an SDS-PAGE gel, electrophoresised, and blotted to PVDF membrane, which is incubated with cell culture media of the indicated hybridoma cells (1:100 dilution) and visualized by chemiluminescence. Cross-reaction of the antibody produced by the hyridoma cell identified above to the other isoform is also determined. The identified isoform-specific antibody is employed in the methods of the present invention, such as an ALT isoform-specific ELISA.

Differences in ALT isoenzyme in tissue distribution, gene regulation, and possible cellular localization suggest that the ability to measure ALT isoenzyme-specific activity levels is a significant improvement over measurement of total ALT activity in clinical diagnostics. The cloning of murine and *rattus* homologues of human ALT isoenzymes provides a novel tool for clinical applications of ALT isoenzymes as molecular markers for nonalcoholic fatty liver diseases as well as other clinical conditions.

Data herein are generally presented as mean±standard deviation (SD). Statistical significance was determined by Student unpaired t test. P value less than 0.05 was considered significant.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. An isolated and purified alanine transaminase (ALT) polypeptide, wherein the polypeptide is selected from a polypeptide comprising the amino acid sequence of SEQ ID NO: 2 and a polypeptide sequence comprising at least 98% identity to the amino acid sequence of SEQ ID NO: 1.

2. An isolated and purified alanine transaminase (ALT) polypeptide sequence comprising the amino acid sequence of SEQ ID NO: 5.

3. A method of producing the ALT polypeptide of claim 1, comprising:

providing an ALT polynucleotide sequence for the ALT polypeptide of claim 1 in an expression vector;

introducing the expression vector into a host cell such that a recombinant host cell is produced; and subjecting to the recombinant host cell to conditions such that the ALT polypeptide of claim 1 is expressed.

4. The isolated and purified alanine transaminase (ALT) polypeptide of claim 1, wherein the polypeptide sequence comprises at least 99% identity to the amino acid sequence of SEQ ID NO: 1.

5. The isolated and purified alanine transaminase (ALT) polypeptide of claim 1, wherein the polypeptide comprises the sequence of SEQ ID NO: 1.

* * * * *

UNITED STATES PATENT AND TRADEMARK OFFICE
CERTIFICATE OF CORRECTION

| | | |
|---|---|---|
| PATENT NO. | : 7,914,985 B2 | Page 1 of 1 |
| APPLICATION NO. | : 11/587331 | |
| DATED | : March 29, 2011 | |
| INVENTOR(S) | : Da-Wei Gong et al. | |

It is certified that error appears in the above-identified patent and that said Letters Patent is hereby corrected as shown below:

Column 1, line 6, cancel the text beginning with "This work was supported" to and ending "to this invention." in Column 1, line 8, and insert the following:

--This invention was made with government support under Grant Number DK060563 awarded by the National Institutes of Health. The government has certain rights in the invention.--

Signed and Sealed this

Thirty-first Day of January, 2012

David J. Kappos
*Director of the United States Patent and Trademark Office*

SEQUENCE LISTING

<160> NUMBER OF SEQ ID NOS: 12

<210> SEQ ID NO 1
<211> LENGTH: 496
<212> TYPE: PRT
<213> ORGANISM: Murinae gen. sp.

```
<400> SEQUENCE: 1

Met Ala Ser Gln Arg Asn Asp Arg Ile Gln Ala Ser Arg Asn Gly Leu
1               5                   10                  15

Lys Gly Lys Val Leu Thr Leu Asp Thr Met Asn Pro Cys Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Phe Arg Gln Val Leu Ala Leu Cys Val Tyr Pro Asn Leu Leu Ser
                85                  90                  95

Ser Pro Asp Phe Pro Glu Asp Ala Lys Arg Arg Ala Glu Arg Ile Leu
            100                 105                 110

Gln Ala Cys Gly Gly His Ser Leu Gly Ala Tyr Ser Ile Ser Ser Gly
        115                 120                 125

Ile Gln Pro Ile Arg Glu Asp Val Ala Gln Tyr Ile Glu Arg Arg Asp
    130                 135                 140

Gly Gly Ile Pro Ala Asp Pro Asn Asn Ile Phe Leu Ser Thr Gly Ala
145                 150                 155                 160

Ser Asp Ala Ile Val Thr Met Leu Lys Leu Leu Val Ala Gly Glu Gly
                165                 170                 175

Arg Ala Arg Thr Gly Val Leu Ile Pro Ile Pro Gln Tyr Pro Leu Tyr
            180                 185                 190

Ser Ala Ala Leu Ala Glu Leu Asp Ala Val Gln Val Asp Tyr Tyr Leu
        195                 200                 205

Asp Glu Glu Arg Ala Trp Ala Leu Asp Ile Ala Glu Leu Arg Arg Ala
    210                 215                 220

Leu Cys Gln Ala Arg Asp Arg Cys Cys Pro Arg Val Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Gly Leu Phe Leu Met Ala Asp
            260                 265                 270

Glu Val Tyr Gln Asp Asn Val Tyr Ala Glu Gly Ser Gln Phe His Ser
        275                 280                 285

Phe Lys Lys Val Leu Thr Glu Met Gly Pro Pro Tyr Ala Thr Gln Gln
    290                 295                 300

Glu Leu Ala Ser Phe His Ser Val Ser Lys Gly Tyr Met Gly Glu Cys
305                 310                 315                 320

Gly Phe Arg Gly Gly Tyr Val Glu Val Asn Met Asp Ala Glu Val
                325                 330                 335

Gln Lys Gln Met Ala Lys Leu Met Ser Val Arg Leu Cys Pro Pro Val
            340                 345                 350

Pro Gly Gln Ala Leu Met Gly Met Val Val Ser Pro Pro Thr Pro Ser
        355                 360                 365

Glu Pro Ser Phe Lys Gln Phe Gln Ala Glu Arg Gln Glu Val Leu Ala
    370                 375                 380

Glu Leu Ala Ala Lys Ala Lys Leu Thr Glu Gln Val Phe Asn Glu Ala
385                 390                 395                 400

Pro Gly Ile Arg Cys Asn Pro Val Gln Gly Ala Met Tyr Ser Phe Pro
                405                 410                 415
```

```
Gln Ile Gln Leu Pro Leu Lys Ala Val Gln Arg Ala Gln Asp Leu Gly
            420                 425                 430

Leu Ala Pro Asp Met Phe Phe Cys Leu Cys Leu Leu Glu Glu Thr Gly
            435                 440                 445

Ile Cys Val Val Pro Gly Ser Gly Phe Gly Gln Gln Glu Gly Thr Tyr
450                 455                 460

His Phe Arg Met Thr Ile Leu Pro Pro Met Glu Lys Leu Arg Val Leu
465                 470                 475                 480

Leu Glu Lys Leu Arg His Phe His Ala Lys Phe Thr His Glu Tyr Ser
                485                 490                 495

<210> SEQ ID NO 2
<211> LENGTH: 522
<212> TYPE: PRT
<213> ORGANISM: Murinae gen. sp.

<400> SEQUENCE: 2

Met Gln Arg Ala Ala Val Leu Val Arg Arg Gly Ser Cys Pro Arg Ala
1               5                   10                  15

Ser Gly Pro Trp Gly Arg Ser His Ser Ser Ala Ala Glu Ala Ser
            20                  25                  30

Ala Ala Leu Lys Val Arg Pro Glu Arg Ser Pro Arg Asp Arg Ile Leu
            35                  40                  45

Thr Leu Glu Ser Met Asn Pro Gln Val Lys Val Glu Tyr Ala Val
50                  55                  60

Arg Gly Pro Ile Val Leu Lys Ala Gly Glu Ile Glu Met Glu Leu Gln
65                  70                  75                  80

Arg Gly Ile Lys Lys Pro Phe Thr Glu Val Ile Arg Ala Asn Ile Gly
            85                  90                  95

Asp Ala His Ala Met Gly Gln Gln Pro Ile Thr Phe Leu Arg Gln Val
            100                 105                 110

Met Ala Leu Cys Thr Tyr Pro Asn Leu Leu Asn Ser Pro Ser Phe Pro
            115                 120                 125

Glu Asp Ala Lys Lys Arg Ala Arg Arg Ile Leu Gln Ala Cys Gly Gly
            130                 135                 140

Asn Ser Leu Gly Ser Tyr Ser Ala Ser Gln Gly Val Asn Cys Ile Arg
145                 150                 155                 160

Glu Asp Val Ala Ala Phe Ile Thr Arg Arg Asp Gly Val Pro Ala Asp
                165                 170                 175

Pro Asp Asn Ile Tyr Leu Thr Thr Gly Ala Ser Asp Gly Ile Ser Thr
            180                 185                 190

Ile Leu Lys Leu Leu Val Ser Gly Gly Lys Ser Arg Thr Gly Val
            195                 200                 205

Met Ile Pro Ile Pro Gln Tyr Pro Leu Tyr Ser Ala Val Ile Ser Glu
210                 215                 220

Leu Asp Ala Val Gln Val Asn Tyr Tyr Leu Asp Glu Glu Asn Cys Trp
225                 230                 235                 240

Ala Leu Asn Val Asp Glu Leu Arg Arg Ala Leu Trp Gln Ala Lys Asp
            245                 250                 255

His Cys Asp Pro Lys Val Leu Cys Ile Ile Asn Pro Gly Asn Pro Thr
            260                 265                 270

Gly Gln Val Gln Ser Arg Lys Cys Ile Glu Asp Val Ile His Phe Ala
            275                 280                 285

Trp Glu Glu Lys Leu Phe Leu Leu Ala Asp Glu Val Tyr Gln Asp Asn
290                 295                 300
```

Val Tyr Ser Pro Asp Cys Arg Phe His Ser Phe Lys Lys Val Leu Tyr
305                 310                 315                 320

Gln Met Gly His Glu Tyr Ser Ser Asn Val Glu Leu Ala Ser Phe His
            325                 330                 335

Ser Thr Ser Lys Gly Tyr Met Gly Glu Cys Gly Tyr Arg Gly Gly Tyr
            340                 345                 350

Met Glu Val Ile Asn Leu His Pro Glu Ile Lys Gly Gln Leu Val Lys
        355                 360                 365

Leu Leu Ser Val Arg Leu Cys Pro Pro Val Ser Gly Gln Ala Ala Met
    370                 375                 380

Asp Ile Val Val Asn Pro Pro Glu Pro Gly Glu Glu Ser Phe Glu Gln
385                 390                 395                 400

Phe Ser Arg Glu Lys Glu Phe Val Leu Gly Asn Leu Ala Lys Lys Ala
            405                 410                 415

Lys Leu Thr Glu Asp Leu Phe Asn Gln Val Pro Gly Ile Gln Cys Asn
            420                 425                 430

Pro Leu Gln Gly Ala Met Tyr Ala Phe Pro Arg Ile Leu Ile Pro Ala
        435                 440                 445

Lys Ala Val Glu Ala Ala Gln Ser His Lys Met Ala Pro Asp Met Phe
    450                 455                 460

Tyr Cys Met Lys Leu Leu Glu Glu Thr Gly Ile Cys Val Val Pro Gly
465                 470                 475                 480

Ser Gly Phe Gly Gln Arg Glu Gly Thr Tyr His Phe Arg Met Thr Ile
            485                 490                 495

Leu Pro Pro Val Asp Lys Leu Lys Thr Val Leu His Lys Val Lys Asp
            500                 505                 510

Phe His Leu Lys Phe Leu Glu Gln Tyr Ser
            515                 520

<210> SEQ ID NO 3
<211> LENGTH: 1770
<212> TYPE: DNA
<213> ORGANISM: Murinae gen. sp.

<400> SEQUENCE: 3
cccacgcgtc cggtgcctta cctcacgcag actccccatt cccagccctg ctccccaact     60 ggaccccttct tcttgagcca gcattcttgc ctgctttgag cagccatggc ctcacaaagg    120
aatgaccgga tccaggcttc aaggaatgga ctgaagggga aggtgctaac tctggatacc    180
atgaacccat gtgtgcggag ggtggagtat gcagtccgag gccccatcgt gcaacgtgcc    240
ttggagctgg agcaggagct gcgccagggt gtgaagaagc cttttactga ggttatccgt    300
gccaatattg gggatgcaca agccatgggg cagagaccca tcaccttctt ccgccaggtc    360
ctggccctct gtgtctaccc caatcttctg agcagtccgg acttcccaga ggatgccaag    420
agaagggcag aacgcatctt gcaggcatgc gggggccaca gcctgggtgc ctatagcatt    480
agctctggaa tccagccgat tcgggaggat gtggcgcaat atattgagag gagagacgga    540
ggcatccctg cagacccgaa caacatattt ctgtccacag gggccagcga tgccatcgtg    600
accatgctca gctgctggt agccggcgag ggccgtgcgc gaaccggtgt actcattccc    660
attcctcagt acccactgta ctcagctgcg ctggctgagc tggacgccgt gcaagtggac    720
tactacctgg acgaagagcg cgcctgggct cttgacatcg ctgagctgcg gcgcgctctg    780
tgccaggcac gtgaccgctg ctgccctcga gtactatgcg tcatcaaccc cggcaacccc    840
acggggcagg tgcagacccg tgaatgcatc gaggccgtaa tccgctttgc tttcgaagag    900

```
ggactcttcc tgatggctga tgaggtatac aagacaatg tatatgccga gggctctcag    960
ttccattcat tcaagaaggt gctcacggag atggggccac catatgccac gcagcaggag   1020
ctcgcgtctt tccactcagt ctctaagggc tacatgggcg agtgcgggtt cgtggtggc    1080 tatgtggaag tggtaaacat ggatgccgag gtgcagaaac agatggcgaa actgatgagc   1140
gtgcggttgt gtccaccagt gccgggccag gctttgatgg catggtggt cagtccgcca    1200 accccctcgg agccgtcctt caagcagttt caagcagaga ggcaggaggt gctggctgaa   1260
ctggcagcca aggctaaact cacggagcag gtcttcaacg aggcccccgg gatccgctgc   1320
aacccggtgc agggcgctat gtattccttc cctcaaattc agctgccttt gaaagcagtg   1380
cagcgtgcgc aggacctggg cctggcccct gacatgttct tctgtctgtg cctcctggaa   1440
gagactggca tctgcgttgt gcctgggagt ggctttgggc agcaggaggg cacctatcat   1500
ttccggatga ccattctgcc ccccatggag aaactgcggg tgctgctgga gaaactgagg   1560
cacttccatg ctaaattcac tcatgagtac tcctgaagcc actgctaggg ccacactgga   1620
tgctctctga ctcaacaaac tgagggtcct tgggagccct cactatttct gattttgcat   1680
agggtctggg tacttgtccc tgcaggtccc taataaagct gggtgtaggc ctgatttgag   1740
gtggctgcct gggtgacccc aaaaaaaaaa                                   1770

<210> SEQ ID NO 4
<211> LENGTH: 3620
<212> TYPE: DNA
<213> ORGANISM: Murinae gen. sp.

<400> SEQUENCE: 4
ggaggtgctg gtgccaggcg ccaggatgcg gtggccggcc accgggtttg ggagcagccc     60
aggctcacct taaccggagc ggtgcggacg gtcccgcggc gacagggcta atctcggcag    120
gttcgcgatg cagcgggcag cggtgctggt gcggcgggc tcctgccccc cgcgcctcggg   180 cccctggggc cgtagtcaca gcagcgctgc agccgaagcc tcgcggcgc tcaaggtgcg    240 accggagcgc agccctcgag accgcatcct caccctggag tccatgaacc cgcaggtgaa    300
ggcggtggag tacgctgtgc ggggaccat cgtgctcaaa gccggcgaga tcgagatgga    360
gctgcagcgg gtatcaaaa aaccattcac tgaggtaatc cgagccaaca ttggggatgc    420
ccatgctatg ggccagcagc caatcaccttt cctccgtcag gtgatggcac tctgcaccta    480
cccaaaccta ctaaacagcc ccagcttccc agaagacgct aagaaacgag cgcggcggat    540
cctgcaggct tgtggtggaa acagcttggg atcttacagt gctagccagg gcgttaactg    600
tatccgtgaa gatgtggcag cctttatcac caggagagat ggtgtgcctg cagacccaga    660
caacatttac ctgactactg gagctagcga cggtatttct acaatcctga aactcctggt    720
ctccggtggt ggcaagtcac ggaccggcgt gatgattccc atcccccagt atcccttgta    780
ctccgcggtc atctccgagc tcgacgcggt gcaggtcaac tactatctgg atgaagagaa    840
ctgctgggct ttgaatgtgg acagctccg gcgggcattg tggcaagcca agaccactg     900 tgaccctaaa gttctctgca ttatcaaccc cggaaacccc acaggccagg tacaaagcag    960
aaagtgcata gaagatgtga ttcacttttgc ctgggaagag aagctttttc tcctggctga   1020
tgaggtgtac caggacaacg tgtactctcc agactgcaga ttccactcct ttaagaaagt   1080 gcttttaccag atggggcacg agtactccag caacgtggag ctcgcctcct tccactccac   1140
ctccaagggc tacatgggcg agtgtggcta cagagggggc tacatggagg tgatcaattt    1200
gcaccccgag atcaaaggcc agctggtgaa gctactctcg gttcgcctct gtccgccagt   1260
```

```
gtcaggacag gccgccatgg acattgttgt gaatccacca gaaccaggag aggagtcctt    1320
tgagcaattc agcagggaaa agaattcgt ccttggtaat ctggccaaaa aagcaaagct     1380
gacagaagat ctgtttaacc aagtcccagg gatccagtgc aacccttgc aaggagctat    1440 gtatgcgttc cctcggattc tcatccctgc caaggccgtg gaggcagctc agtcccataa    1500
aatggctcca gacatgttct actgcatgaa gctcctggag gagactggca tctgtgtcgt    1560
gcctggcagt ggctttgggc agcgagaagg cacttaccac ttcagaatga ccattctccc    1620
tccggtggat aaactgaaga ccgtgctcca caaggtgaaa gactttcacc tgaagttcct    1680
ggagcagtac tcatgaggac gcctcaggca ccggagccag accctcccaa gaccacccag    1740
gccttcctca aggactctgc ctcagacctc agacaggcca ccaacgctgt tcatcttcat    1800
ttccccaagg agacttcttt ctttgtgcct tgatgtttga gagttcttcg agcaaacagt    1860
ggttttgcaa tgtctcacag gccctgtttt tgttttgttt tgtttttgttc ttttttttaaa  1920 tgcaaccaaa gtagagtcaa cctgctcggc agatgtactt ggattctctg aatcgctatt    1980
ctgtttggag agttcctttg ggttttaagc agccagagta catggaaatg agattatgtc    2040
agatctggag aaacaagcag gtgttgggaa atatgtgact tgacatgata agggctggga    2100
atccagaaat caatagtgag atccatgaaa tcaaaccctg accagtgtgg aaatgtagcc    2160
ttttggacag taagcctgca agtctagtga gaactcagaa aaagctgacc attctggtct    2220
gaagataggc agcgcatcac aggcaagaat atcgaagtca gtagtaggac aggggtcaca    2280
tcagatacca gctcaaattg cactagctat ctagaacagt tttctccagg tttgcctgag    2340
ccttgatgca taccatcgcc ctctgctggt cgcagcagag ataagcaagg gctgaaaatg    2400
gaggcaatcc tttcccaagg ccctgaaagt tgttttttcat ggtttcaaac tgaatttggc   2460
tcatttgtaa ctaactgatc acggtgcctg gttacactgg ctgccaagaa ggaggcatgc    2520
aatctgattc agtgctctct tcacatcagt ttcctgcctc cctccctcat ctgcggacag    2580
catcctatct catcaggctt ccctgtgtgt cacaaagtag cagccaccaa gcaaatatat    2640
tccttgaatt agcacacctg ggtgggccat gtgcgcacca aggaaacagg tgctataggg    2700
agcgccaggt caggcttgtc tcttaactgt ctccgttctt cagtgagcgt gggaaagctg    2760
tcgggagctc ccgcgcagga gcctgggtac ccacgcagtg agtcaaggga gttttcggag    2820
ccagagagag aacgatgtga aggctgtgga gtaaggctga aaccagcttc ctgccctata    2880
gtcccacact gcaggggtg cgactttaaa acagaacttc aagttgttaa cactcacaag     2940
cattgcatta ctgtgaagga agtagccgca tccataatag gatgtgacgg tctacagctt    3000
ttcctttaaa agctgaaaag gtaccatgtg tgctcgctag gcatataatc cagatatgct    3060
ccagagttct gagattcttc catgaaaggt taactagaag ctagaatatt tttttatatt    3120
tttgtaacaa ttggctttttt tcatgggggg aggggagtag agggttagta tttatagtcc   3180
taacaagtcc aaaaatttttt ataagtgtct tcagattata aataaccctc caaattttgc   3240 aatgttaca tgtttttttt ttaagatgac aaatatgctt gatttgcttt ttaaataaaa     3300
gtttagctgt tctaagagat taacttcaag taggatggct ggttatgata gtttggattt    3360
tctacaggtt ctgttgccat gccttttggg tttcagcatc actcgagccg cagcatgtgg    3420
gtggggctgt ggaaacctgg ccaggctgga cctggtcagc cacacctcag agacattgtt    3480
tccatttgga tgtgagcagg cgcaggcctg catgctcttt cctacttagc atcatcagtt    3540
cttccgcctc cttagcatgg ttcttttgtaa cagccatgct gggaagctct gaacaataaa    3600
atacttccag agtggtgaaa                                                 3620
```

<210> SEQ ID NO 5
<211> LENGTH: 522
<212> TYPE: PRT
<213> ORGANISM: Rattus sp.

<400> SEQUENCE: 5

```
Met Gln Arg Ala Ala Val Leu Val Arg Gly Ser Cys Pro Arg Ala
1               5                   10                  15

Ser Gly Pro Trp Gly Arg Ser His Ser Ser Ala Ala Glu Ala Ser
                20                  25                  30

Ala Ala Leu Lys Val Arg Pro Glu Arg Ser Pro Arg Asp Arg Ile Leu
            35                  40                  45

Thr Leu Glu Ser Met Asn Pro Gln Val Lys Ala Val Glu Tyr Ala Val
50                  55                  60

Arg Gly Pro Ile Val Leu Lys Ala Gly Glu Ile Glu Met Glu Leu Gln
65                  70                  75                  80

Arg Gly Ile Lys Lys Pro Phe Thr Glu Val Ile Arg Ala Asn Ile Gly
                85                  90                  95

Asp Ala His Ala Met Gly Gln Gln Pro Ile Thr Phe Leu Arg Gln Val
            100                 105                 110

Met Ala Leu Cys Thr Tyr Pro Asn Leu Leu Asn Ser Pro Ser Phe Pro
        115                 120                 125

Glu Asp Ala Lys Lys Arg Ala Arg Arg Ile Leu Gln Ala Cys Gly Gly
    130                 135                 140

Asn Ser Leu Gly Ser Tyr Ser Ala Ser Gln Gly Val Asn Cys Ile Arg
145                 150                 155                 160

Glu Asp Val Ala Ala Phe Ile Thr Arg Arg Asp Gly Val Pro Ala Asp
                165                 170                 175

Pro Asp Asn Ile Tyr Leu Thr Thr Gly Ala Ser Asp Gly Ile Ser Thr
            180                 185                 190

Ile Leu Lys Leu Leu Val Ser Gly Gly Lys Ser Arg Thr Gly Val
        195                 200                 205

Met Ile Pro Ile Pro Gln Tyr Pro Leu Tyr Ser Ala Val Ile Ser Glu
    210                 215                 220

Leu Asp Ala Ile Gln Val Asn Tyr Tyr Leu Asp Glu Asp Asn Cys Trp
225                 230                 235                 240

Ala Leu Asn Val Asp Glu Leu Arg Arg Ala Leu Arg Gln Ala Lys Asp
                245                 250                 255

His Cys Asp Pro Lys Val Leu Cys Ile Ile Asn Pro Gly Asn Pro Thr
            260                 265                 270

Gly Gln Val Gln Ser Arg Lys Cys Ile Glu Asp Val Ile His Phe Ala
        275                 280                 285

Trp Glu Glu Lys Leu Phe Leu Leu Ala Asp Glu Val Tyr Gln Asp Asn
    290                 295                 300

Val Tyr Ser Pro Asp Cys Arg Phe His Ser Phe Lys Lys Val Leu Tyr
305                 310                 315                 320

Gln Met Gly Pro Glu Tyr Ser Ser Asn Val Glu Leu Ala Ser Phe His
                325                 330                 335

Ser Thr Ser Lys Gly Tyr Met Gly Glu Cys Gly Tyr Arg Gly Gly Tyr
            340                 345                 350

Met Glu Val Ile Asn Leu His Pro Glu Ile Lys Gly Gln Leu Val Lys
        355                 360                 365

Leu Leu Ser Val Arg Leu Cys Pro Pro Val Ser Gly Gln Ala Ala Met
    370                 375                 380
```

```
Asp Ile Val Val Asn Pro Pro Val Pro Gly Glu Ser Phe Glu Gln
385                 390                 395                 400

Phe Thr Arg Glu Lys Glu Ser Val Leu Gly Asn Leu Ala Lys Lys Ala
            405                 410                 415

Lys Leu Thr Glu Asp Leu Phe Asn Gln Val Pro Gly Ile Gln Cys Asn
            420                 425                 430

Pro Leu Gln Gly Ala Met Tyr Ala Phe Pro Arg Ile Leu Ile Pro Ala
            435                 440                 445

Lys Ala Val Glu Ala Ala Gln Ser His Lys Met Ala Pro Asp Met Phe
            450                 455                 460

Tyr Cys Met Lys Leu Leu Glu Glu Thr Gly Ile Cys Val Val Pro Gly
465                 470                 475                 480

Ser Gly Phe Gly Gln Arg Glu Gly Thr Tyr His Phe Arg Met Thr Ile
            485                 490                 495

Leu Pro Pro Val Glu Lys Leu Lys Thr Val Leu His Lys Val Lys Asp
            500                 505                 510

Phe His Leu Lys Phe Leu Glu Lys Tyr Ser
            515                 520

<210> SEQ ID NO 6
<211> LENGTH: 496
<212> TYPE: PRT
<213> ORGANISM: Rattus sp.

<400> SEQUENCE: 6

Met Ala Ser Arg Val Asn Asp Gln Ser Gln Ala Ser Arg Asn Gly Leu
1               5                   10                  15

Lys Gly Lys Val Leu Thr Leu Asp Thr Met Asn Pro Cys Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Phe Arg Gln Val Leu Ala Leu Cys Val Tyr Pro Asn Leu Leu Ser
                85                  90                  95

Ser Pro Asp Phe Pro Glu Asp Ala Lys Arg Arg Ala Glu Arg Ile Leu
            100                 105                 110

Gln Ala Cys Gly Gly His Ser Leu Gly Ala Tyr Ser Ile Ser Ser Gly
            115                 120                 125

Ile Gln Pro Ile Arg Glu Asp Val Ala Gln Tyr Ile Glu Arg Arg Asp
130                 135                 140

Gly Gly Ile Pro Ala Asp Pro Asn Asn Ile Phe Leu Ser Thr Gly Ala
145                 150                 155                 160

Ser Asp Ala Ile Val Thr Met Leu Lys Leu Leu Val Ser Gly Glu Gly
            165                 170                 175

Arg Ala Arg Thr Gly Val Leu Ile Pro Ile Pro Gln Tyr Pro Leu Tyr
            180                 185                 190

Ser Ala Ala Leu Ala Glu Leu Asp Ala Val Gln Val Asp Tyr Tyr Leu
            195                 200                 205

Asp Glu Glu Arg Ala Trp Ala Leu Asp Ile Ala Glu Leu Arg Arg Ala
            210                 215                 220

Leu Cys Gln Ala Arg Asp Arg Cys Cys Pro Arg Val Leu Cys Val Ile
225                 230                 235                 240
```

```
Asn Pro Gly Asn Pro Thr Gly Gln Val Gln Thr Arg Glu Cys Ile Glu
                245                 250                 255
Ala Val Ile Arg Phe Ala Phe Lys Glu Gly Leu Phe Leu Met Ala Asp
            260                 265                 270
Glu Val Tyr Gln Asp Asn Val Tyr Ala Glu Gly Ser Gln Phe His Ser
        275                 280                 285
Phe Lys Lys Val Leu Met Glu Met Gly Pro Pro Tyr Ser Thr Gln Gln
    290                 295                 300
Glu Leu Ala Ser Phe His Ser Val Ser Lys Gly Tyr Met Gly Glu Cys
305                 310                 315                 320
Gly Phe Arg Gly Gly Tyr Val Glu Val Asn Met Asp Ala Glu Val
                325                 330                 335
Gln Lys Gln Met Gly Lys Leu Met Ser Val Arg Leu Cys Pro Pro Val
            340                 345                 350
Pro Gly Gln Ala Leu Met Asp Met Val Val Ser Pro Pro Thr Pro Ser
        355                 360                 365
Glu Pro Ser Phe Lys Gln Phe Gln Ala Glu Arg Gln Glu Val Leu Ala
    370                 375                 380
Glu Leu Ala Ala Lys Ala Lys Leu Thr Glu Gln Val Phe Asn Glu Ala
385                 390                 395                 400
Pro Gly Ile Arg Cys Asn Pro Val Gln Gly Ala Met Tyr Ser Phe Pro
                405                 410                 415
Gln Val Gln Leu Pro Leu Lys Ala Val Gln Arg Ala Gln Glu Leu Gly
            420                 425                 430
Leu Ala Pro Asp Met Phe Phe Cys Leu Cys Leu Leu Glu Glu Thr Gly
        435                 440                 445
Ile Cys Val Val Pro Gly Ser Gly Phe Gly Gln Gln Glu Gly Thr Tyr
    450                 455                 460
His Phe Arg Met Thr Ile Leu Pro Pro Met Glu Lys Leu Arg Leu Leu
465                 470                 475                 480
Leu Glu Lys Leu Ser His Phe His Ala Lys Phe Thr His Glu Tyr Ser
                485                 490                 495

<210> SEQ ID NO 7
<211> LENGTH: 1744
<212> TYPE: DNA
<213> ORGANISM: Rattus sp.

<400> SEQUENCE: 7
ctgcagtgtg aagggtgttg tcttacctct cgcagacttt cccattccca gccctgattt      60
ccccactgga cccttctcct tctgaaccag catcctgcct ggtttgagca gtcatggcct     120
cacgggtgaa tgatcaaagc caggcttcaa ggaatgggct gaagggaaag gtgctaactc     180
tggacactat gaacccatgt gtgcggaggg tggagtatgc agttcgagga cccattgtgc     240
agcgtgcctt ggagctggag caggagctgc gtcaggtgt gaagaagccg tttactgagg     300
tcatccgtgc caacattggg gatgcacaag ccatggggca gagacccatc accttcttcc     360
gccaggtcct ggccctctgt gtctacccca atcttctgag cagtcctgac ttcccagagg     420
atgccaagag aagggcagaa cgcatcttgc aggcctgcgg ggccacagc ctgggtgcct     480
atagcattag ctctggaatc cagccgatcc gggaggatgg ggcgcaatac attgagagaa     540
gagacggagg catccccgca gacccgaaca acatatttct atccacaggg gccagcgatg     600
ccatcgtgac aatgctcaag ctgctggtat ctggcgaggg ccgtgcacga acaggtgtac     660
tcattcccat tcctcagtac ccactgtact cagccgcgct ggctgaactg gacgccgtgc     720
```

```
aagtggacta ctacctggac gaagagcgcg cctgggctct ggacatcgca gagctgcggc      780
gcgctctgtg ccaggcacgt gaccgttgct gccctcgagt actgtgcgtc atcaaccccg      840
gcaaccccac tgggcaggtg cagacccgtg agtgcatcga ggccgtaatc cgctttgctt      900
tcaaagaagg actcttcttg atggctgatg aggtatacca ggacaacgtg tatgccgagg      960
gctctcagtt ccattcattc aagaaggtgc tcatggagat ggggccaccg tattccacgc     1020
agcaggagct tgcttctttc cactcagtct ctaagggcta catgggcgag tgcgggtttc     1080
gtggtggcta tgtggaggtg gtaaacatgg atgctgaggt gcagaaacag atggggaagc     1140
tgatgagtgt gcggctgtgt ccaccagtgc caggccaggc cttgatggac atggtggtca     1200
gtccgccaac ccctccgag ccgtccttca agcagtttca agcagagaga caggaggtgc      1260
tggctgaact ggcagccaag gctaagctca cggagcaggt cttcaatgag gctcccggga     1320
tccgctgcaa cccagtgcag ggcgccatgt attccttccc tcaagtgcag ctgcccttga     1380
aagcggtgca gcgtgctcag gaactgggcc tggcccctga catgttcttc tgcctgtgcc     1440
tcctggaaga gactggcatc tgcgttgtgc ccgggagtgg ctttgggcag caggagggca     1500
cctatcattt ccggatgacc attctgcccc ccatggagaa actgcggctg ctgctggaaa     1560
aactcagtca cttccatgcc aagttcaccc atgagtactc ctgaagccac tgctagggcc     1620
acactggaca gtctctgacg caacaaaccg agggtcctta ggaaccctca gtatttctga     1680
ttttgtctag ggtctcggta actgtcctgc gggtccctaa taaatctgat gtcagcctga     1740
aaaa                                                                  1744
```

<210> SEQ ID NO 8
<211> LENGTH: 4838
<212> TYPE: DNA
<213> ORGANISM: Rattus sp.

<400> SEQUENCE: 8

```
cagaattctc acactggttc cctggcctgt ggagtgaggg ctattatggc tgggaaggct       60
aaatggaagc ccttagagct gcctctgcca aagaaaatag tgagccaaaa ccagtattgt      120
attcctggag gaactgcaga aattacacct ccatcaagga cttgaaagat gcagggtggt      180
ggttcccaca tctcccttta actctctatc tggccagtgc agaagacaga tggatcatgg      240
agaatgacag ctgactattg aaagctaaac cagggttaac ctcggaagat tcgcgatgca      300
gcgggcagcg gtgctggtgc ggcgggggctc ctgcccccgc gcctcgggcc cctgggccg      360 tagtcacagc agcgctgcag ccgaagcctc ggcggcgctc aaggtgcgac cagagcgtag      420
ccctcgagac cgcatcctca ccctggagtc catgaacccg caggtgaagg ccgtggagta      480
cgctgtgcgg ggacccatcg tgctcaaggc cggcgagatc gagatggagc tgcagcgggg      540
tatcaaaaaa ccattcactg aggtaatccg agccaacatt ggggatgccc atgctatggg      600
ccagcagcca atcaccttcc ttcgtcaggt gatggctctc tgcacctacc cgaacctgct      660
aaacagcccc agcttcccgg aagatgctaa gaagcgagcg cggcggatcc tgcaggcttg      720
cggtggaaac agcctggggt cttacagtgc gagccagggc gttaactgta tccgagagga     780
cgtggcagcc tttatcacca ggagagatgg tgtacctgca gacccagaca acatttacct      840
gactactgga gcgagcgacg gtatttctac gatcctgaag ctcctggtct ccggcggtgg      900
caagtcacgg accggggtga tgatccccat cccacagtac cccttgtact ccgcggtcat      960
ctccgagctc gacgccatcc aggtgaacta ctatctggat gaggacaact gctgggcttt     1020
gaacgtggac gagctccggc gggcactgcg gcaagctaaa gaccactgtg accctaaagt     1080
```

```
tctctgcatc atcaaccccg gaaacccac aggccaggta caaagcagaa agtgcataga    1140
agatgtgatt cactttgcct gggaagagaa gcttttctc ctggctgacg aggtatacca    1200
ggacaacgtg tactctccgg actgcagatt ccactccttt aagaaagtgc tttaccagat   1260
ggggcctgag tactcgagta atgtggagct tgcctccttc cactccacct ccaagggcta   1320
catgggcgaa tgcggctaca gaggaggcta catggaggtg atcaatttgc accccgagat   1380
caaaggccag ctggttaagc tcctctcggt ccgcctctgt ccgccagtgt ctggacaggc   1440
cgcgatggac attgttgtga atccaccggt gccaggagag gagtcctttg agcaattcac   1500
cagggaaaaa gaatccgtcc ttggtaatct ggccaaaaaa gcaaagctga cagaagatct   1560
gtttaaccaa gtcccgggga tccagtgcaa ccccttgcaa ggagccatgt atgcattccc   1620
tcggattctc atccctgcca aggccgtgga ggcagctcag tcccataaaa tggctccaga   1680
tatgttttac tgcatgaaac tcctggaaga aactggcatc tgtgtcgtgc ctggcagtgg   1740 cttttggacag cgagaaggca cctaccactt cagaatgaca attctccctc cagtggagaa   1800
actgaagaca gtactccaca aggtgaaaga ttttcacctg aagttcctgg agaagtactc   1860
atgaggatgc ctctgcacca gagagagacc ccaataccac ccaggccttc ctcatggact   1920
ctgcctcaga cctcatgcag gtcaccaacc ctgttcatca tcattttcca aggagacttc   1980
tttctttgtg ccttgatgtt cgagagttct tctgagcaaa cagtgatttt gcaatgtcaa   2040 aaaaaaaaa aaaaaaaaa aaaaaaagg gcggccgccc tttttttttt ttttttttt     2100 ttttttttaa ccgtctttta gaggctgacc cagtgaccaa tccgcagaga cacgggaaaa   2160
agatggagtg acgtcgccta ggggcggagc caaggctgct taggggggcgg gcgtttgaaa  2220 ccggtgcttc atagtcgacc ccaaatatca tcttgtgcct ttgagaacca attacttaat   2280
ctctcttgcg tcttttcctt tcccgacccc ctcccagact cttttcgctgc ggttctgcga  2340 ggacggaagg cgccaggagc cggtccgcgt ctcgcaagcg ttgagatctg aggagagctt   2400
gccaactgac cgacccaacg gctcctgctc ctcagtagac cccgcagcct agggactaga   2460
gttgtcactt aagtggatat gaagaaggcg caaataagta cggggggcagc cacgagcttt    2520 ccaaagatta tattttagtc acatccctga agagattctg ctgcacccgt ctctgcaatc   2580
cagtagacaa cgagaggaaa gaaccaggtt ccaactgaac atgtgagagt ctggggctcc   2640
ctgactgagc tgatgcccag agtgctggat ctgggttagt cagcaaccta acaaaagcta   2700 gtccatcac acgcacagaa gccgtcagga cactcggcta catcacacac acagcaattc   2760
tttttgtaaa atcctgcttc ctcaatcctg tgtatatatt ggattttggt gtttaagttg   2820
aagctatgaa gactaagtcc acctgtgctc agaatccaaa ttgcagcata atgatatttc   2880
gtccaaccaa agaagagttt aacgactttg acaaatacat cgcctacatg gagtcccaag   2940
gggcacacag agctggactg gccaaggtca tcccgccaaa agaatggagg gccaggcagt   3000
cttatgacaa tatcagtaac atcttaatag caactcccct gcagcaagta gtctccgggc   3060
aggcaggtgt gttcactcaa taccataaga agaagaaagc catgacagtt gggcagtacc   3120
ggcacctggc caacagtaaa aaataccaaa ccccaccaca cctggatttt gaagatttgg   3180
agagaaaata ctggaagaat cgcctgtatg agtcaccaat ttatggtgct gacgtcagtg   3240
gctccctgtt tgatgggaag actcaacagt ggaatgtggg ccacctggga acaattcaag   3300
acctattgga acaggaatgc ggcatagtga ttgagggcgt caacacgccc tacctgtact   3360
ttggcatgtg gaagacctcc tttgcgtggc acacggagga catggacctg tacagtatca   3420
actacctgca cttggacag cccaagacct ggtatgctgt acccctgag catggcaggc     3480
```

```
gcctggagct cctagccaag gaactcttcc caggcagctc ccagggctgc caggccttcc    3540
tgaggcacaa ggtggcgctc atctcaccca ctgtgctcaa ggagaatggc atccctttg    3600 gtcgaatcac ccaggaggct ggggagttca tggtcacctt tccctatggc taccacgcgg    3660
gcttcaacca tggcttcaac tgtgcagaag ccatcaattt cgccacgccg aggtggattg    3720
actatggcaa ggtggcatct cagtgcagct gtggggaggc cagggtgagc ttctccatgg    3780
atgcctttgt gaggatcctg cagcctgagc gatatgagat gtggaaacga ggtcaagatc    3840
aggcagttgt ggaccacaca gaggctatgg ggcctaccag tcaggagctc accacctggc    3900
gggtgatcca ggcaccaaga aaaacttggg gcctgaagca tctccggctt cgccaggttt    3960
cacgctgtct tctgcctgta gccactgaca gtaacattgc caacaacacc cagatgtgcc    4020
acacctccag gcaagcagca gattcgaaag gtgatgaggt ccaggagtct gacccagcca    4080
tagccccacc atatcctctg ggtctatctt ctcctggcca catgtcaact ggaaaacgtg    4140
gtcttggtcg tcgcccttgt gaactaggag ttcaggagtc caccaatgga gctccagtca    4200
agaggcgact tccagaaggc agagatgaca gaagtcccag cccagagctt cagtcccagt    4260
ccgtgactgg agacttaata gtcaactcag accttgtaaa tcctgggcca cagcatcctg    4320
tgacagcttc tgaaggggga ttgacctctg accctaaac ctatgtcctg acttacagct    4380
cattgccccg cactcaggat gctctctaag gccattacct cagttttgac tgagtttgca    4440
gggcactggc tacacctgag agagttcctt gtcagttcta actcctaaac acccctgcc    4500 ccttcctcct tccggaactc ggccagctct ggatactgct aactcctgct cttccaggag    4560
atatttcatt ggctgctcct tttgagtttc tgagagccaa gttcagctga gactgctcag    4620
tgctcatctt ccctccctct gccatttctt gcaaatgtct aactgttgac actagatgac    4680
tactcacaaa ggaagtagtc acaaaaagg tcaaagtca tttgagagtc acagatgatc    4740
tctcaaactt gatgtattaa aatgtgtctc acccggcttt cacaaataaa ggcaaagcag    4800
tcaaaagctt aaaaaaaaaa aaaaaaaaa aaaaaaaa                            4838

<210> SEQ ID NO 9
<211> LENGTH: 33
<212> TYPE: DNA
<213> ORGANISM: Homo sapiens

<400> SEQUENCE: 9
ggaagatctc atatggcctc acaaaggaat gac                                 33

<210> SEQ ID NO 10
<211> LENGTH: 32
<212> TYPE: DNA
<213> ORGANISM: Homo sapiens

<400> SEQUENCE: 10
aatgcggccg ctcaggagta ctcatgagtg aa                                  32

<210> SEQ ID NO 11
<211> LENGTH: 43
<212> TYPE: DNA
<213> ORGANISM: Homo sapiens

<400> SEQUENCE: 11
ggaagatctc catggcccat atgcagcggg cagcggtgct ggt                      43

<210> SEQ ID NO 12
<211> LENGTH: 32
```

```
<212> TYPE: DNA
<213> ORGANISM: Homo sapiens

<400> SEQUENCE: 12
aatgcggccg ctcatgagta ctgctccagg aa                                    32
```